(12) United States Patent
Prato et al.

(10) Patent No.: US 9,556,238 B2
(45) Date of Patent: Jan. 31, 2017

(54) MAGNETOSOME GENE EXPRESSION IN EUKARYOTIC CELLS

(75) Inventors: Frank S Prato, London (CA); Donna E Goldhawk, London (CA); Cheryl R McCreary, Balzac (CA); Rebecca McGirr, London (CA); Savita Dhanvantari, London (CA); Terry R Thompson, London (CA); Alex W Thomas, London (CA); David Hill, London (CA)

(73) Assignee: Multi-Magnetics Inc., London (CA)

( * ) Notice: Subject to any disclaimer, the term of this patent is extended or adjusted under 35 U.S.C. 154(b) by 378 days.

(21) Appl. No.: 12/303,793

(22) PCT Filed: Jun. 8, 2007

(86) PCT No.: PCT/CA2007/001016
§ 371 (c)(1),
(2), (4) Date: Mar. 10, 2009

(87) PCT Pub. No.: WO2007/140617
PCT Pub. Date: Dec. 13, 2007

(65) Prior Publication Data
US 2010/0297022 A1 Nov. 25, 2010

Related U.S. Application Data

(60) Provisional application No. 60/811,784, filed on Jun. 8, 2006, provisional application No. 60/879,791, filed on Jan. 11, 2007.

(51) Int. Cl.
| | | |
|---|---|---|
| *A61K 49/06* | (2006.01) | |
| *A61K 35/12* | (2015.01) | |
| *C12N 15/63* | (2006.01) | |
| *C12N 5/10* | (2006.01) | |
| *C12N 1/00* | (2006.01) | |
| *C07K 14/195* | (2006.01) | |
| *A61K 49/14* | (2006.01) | |
| *A61K 49/18* | (2006.01) | |

(52) U.S. Cl.
CPC .......... *C07K 14/195* (2013.01); *A61K 49/14* (2013.01); *A61K 49/1806* (2013.01); *A61K 49/1896* (2013.01); *C12N 2510/00* (2013.01)

(58) Field of Classification Search
CPC ............................ C12N 2510/00; A61K 49/14
See application file for complete search history.

(56) References Cited

U.S. PATENT DOCUMENTS

2004/0048289 A1* 3/2004 Matsunaga et al. ............... 435/6
2009/0311194 A1* 12/2009 Hu ..................... A61K 49/1818
424/9.321

FOREIGN PATENT DOCUMENTS

JP 62275679 A 11/1987
WO WO 2006119102 11/2006

OTHER PUBLICATIONS

Okamura et al (Applied and Environmental Microbiology. Jul. 2003; 69(7): 4274-4277).*
Matsunaga et al. (Journal of Bacteriology, May 1992; 174(9): 2748-2753).*
Sambrook et al. (Molecular Cloning: a laboratory manual, 2nd ed. Cold Spring Harbor Laboratory Press, Cold Spring Harbor, NY).*
Genove et al. (Nature Medicine. Apr. 2005; 11(4): 450-454).*
Xu et al (Nature Biotechnology. Oct. 2001; 19: 971-974).*
Yoshino et al. (Applied and Environmental Microbiology. American Society for Microbiology. May 2004; 70(5): 2880-2885).*
Roger Tsien (Nature Reviews Molecular Cell Biology 4, SS16-SS21 (2003)).*
Butleand et al. (Physics and Chemistry Basis of Biotechnology: Focus on Biotechnology. vol. 7, 2002; "Molecular and Cellular Magnetic Resonance Contrast Agents," 191-2011).*
Lumelsky et al. (Science. May 18, 2001; 292:1389-1394).*
Martinez et al. (Cancer. Jan. 15, 1996; 77(2): 409-419).*
Brennan et al. (AJR. Sep. 2005; 185: 711-716).*
Moore et al (Radiology. Oct. 2001. 221: 244-250).*
Gorby et al. (Journal of Bacteriology. Feb. 1988; 170(2): 834-841).*
Nimes Nathan et al: "In vivo MRI of embryonic stem cells in a mouse model of myocardial infarction" Magnetic Resonance in Medicine, vol. 52, No. 5, Nov. 2004 (Nov. 2004), pp. 1214-1219, XP002529308. ISSN: 0740-3194.
Jasanoff A: "Functional MRI using molecular imaging agents". Trends in Neuroscience, Elsevier, Amsterdam, NL, vol. 28, No. 3, Mar. 1, 2005 (Mar. 1, 2005), pp. 120-126, XP004771624. ISSN: 0166-2236.
Schuler D: "Formation of magnetosomes in magnetotactic bacteria". Journal of Molecular Microbiology and Biotechnology, Horizon Scientific Press, Wymondham, GB, vol. 1, No. 1, Jan. 1, 1999 (Jan. 1, 1999), pp. 79-86, XP003002490. ISSN : 1464-1801.
Oluda Y et al: "Expression and characterization of a magnetosome-associated protein, TPR-containing MAM22, in *Escherichia coli*", FEBS Letters, Elseview, Amsterdam, NL, vol. 491, No. 3, Mar. 2, 2001 (Mar. 2, 2001), pp. 169-173, XP004257297. ISSN: 0014-5793.
Zurika Omar et al: "MagA is sufficient for producing magnetic nanoparticles in mammalian cells, making it an MRI reporter". Magnetic Resonance in Medicine, vol. 59, No. 6, Jun. 2008 (Jun. 2008), pp. 1225-1231, XP002529309. ISSN: 0740-3194. *the whole document*.
Arbab, A., Bashaw, L., Bradley, R., Jordan, E., Bulte, J., and Frank, J. (2003). Intracytoplasmic tagging of cells with ferumoxides and transfection agent for cellular magnetic resonance imaging after cell transplantation: methods and techniques. Transplantation 76, 1123-1130.

(Continued)

*Primary Examiner* — Scott Long
(74) *Attorney, Agent, or Firm* — Ridout & Maybee LLP

(57) ABSTRACT

The invention is the production of magnetosome-like structures in cells. The invention provides in vitro and in vivo diagnostic and therapeutic methods using eukaryotic cells expressing magnetosome-like structures that act as contrast agents.

20 Claims, 24 Drawing Sheets

(56) References Cited

OTHER PUBLICATIONS

Bauerlein, E., Schuler, D., Reszka, R., and Pauser, S. (2001). Specific magnetosome, method for the production and use thereof, U. P. Office, ed. (United States: Max-Delbruck-Centrum fur Molekulare Medizin and Max-PlanckGesellschaft zur Forderung der Wissenschaften E.V.).
Bauerlein, E., Schuler, D., Reszka, R., and Pauser, S. (2002). Magnetosomes, method for making and using, U. P. Office, ed. (United States).
Bazylinski, D., and Frankel, R. (2004). Magnetosome formation in prokaryotes. Nat Rev Microbiol 2, 217-230.
Bulte, J., Douglas, T., Mann, S., Frankel, R., Moskowits, B., Brooks, R., Baumgartner, C., Vymazal, J., and Frank, J. (1994). Magnetoferritin. Biomineralization as a novel molecular approach in the design of iron-oxide-based magnetic resonance contrast agents. Invest Radiol 29 Suppl.2, S214-S216.
Chalfie, M., Tu, Y., Euskirchen, G., Ward, W., and Prasher, D. (1994). Green fluorescent protein as a marker for gene expression. Science 263, 802-805.
Dhanvantari, S., Foster, P., White, D., McCreary, C., Nguyen, B., Mugimba, A., Chan, K., Hoffman, L., McGirr, R., Kovacs, M., and Wells, R. (2006). Cellular and molecular imaging of pancreatic islet cells, in Keystone Symposium, Towards Understanding Islet Biology.
Dhanvantari, S., Tai, J.-H., White, D., Heyn, C., Rutt, B., and Foster, P. (2004). Single cell magnetic resonance imaging of beta cells, in Annual Meeting of the Canadian Diabetes Association.
Genove, G., DeMarco, U., Xu, H., Goins, W., and Ahrens, E. (2005). A new transgene reporter for in vivo magnetic resonance imaging. Nat Med 11, 450-454.
Grünberg, K., Wawer, C., Tebo, B., and Schüler, D. (2001). A large gene cluster encoding several magnetosome proteins is conserved in different species of magnetotactic bacteria. Appl Env Microbiol 67, 4573-4582.
Hautot, D., Pankhurst, Q., Khan, N., and Dobson, J. (2003). Preliminary evaluation of nanoscale biogenic magnetite in Alzheimer's disease brain tissue. Proc R Soc Lond B (Suppl) 270, S62-S64.
Herborn, C., Papanikolaou, N., Reszka, R., Grunberg, K., Schüler, D., and Debatin, J. (2003). Magnetosomes as biological model for iron binding: relaxivity determination with MRI. Rofo: Fortschritte auf dem Gebiete der Rontgenstrahlen und der Nuklearmedizin 175, 830-834.
Hergt, R., Hiergeist, R., Zeisberger, M., Schuler, D., Heyen, U., Hilger, I., and Kaiser, W. (2005). Magnetic properties of bacterial magnetosomes as potential diagnostic and therapeutic tools. J Magn Magn Mater 293, 80-86.
Hilger, I., Fruhauf, K., Andra, W., Hiergeist, R., Hergt, R., and Kaiser, W. (2002). Heating potential of iron oxides for therapeutic purposes in interventional radiology. Acad Radiol 9, 198-202.
Kirschvink, J. (1989). Magnetite biomineralization and geomagnetic sensitivity in higher animals: an update and recommendations for future study. Bioelectromagnetics 10, 239-259.
Kirschvink, J., Kobayashi-Kirschvink, A., and Woodford, B. (1992). Magnetite biomineralization in the human brain. Proc Nat Acad Sci USA 89, 7683-7687.
Kirschvink, J., Walker, M., and Diebel, C. (2001). Magnetite-based magnetoreception. Curr Opin Neurobiol 11, 462-467.
Komeili, A., Li, Z., Newman, D., and Jensen, G. (2006). Magnetosomes are cell membrane invaginations organized by the actin-like protein MamK. Science 311, 242-245.
Lin, H., Blank, M., and Goodman, R. (1999). A magnetic field-responsive domain in the human HSP70 promoter. J Cell Biochem 75, 170-176.
Matsunaga, T. (2000). Protein-bound magnetic particles and process of producing the same, U. S. P. Office, ed. (United States: TDK Corporation).
Matsunaga, T., Nakamura, C., Burgess, J., and Sode, K. (1992). Gene transfer in magnetic bacteria: transposon mutagenesis and cloning of genomic DNA fragments required for magnetosome synthesis. J Bacteriol 174, 2748-2753.
Matsunaga, T., Takeyama, H., and Okamura, Y. (2004). Magnetic particle membrane-specific protein, U. S. P. Office, ed. (United States).
Okamura, Y., Takeyama, H., and Matsunaga, T. (2001) A magnetosome-specific GTPase from the magnetic bacterium Magnetospirillum magneticum AMB-1. J. Biol. Chem. 276, 48183-48188.
Ritz, T., Thalau, P., Phillips, J., Wiltschko, R., and Wiltschko, W. (2004). Resonance effects indicate a radical-pair mechanism for avian magnetic compass. Nature 429, 177-180.
Schüler, D. (Apr. 2004-Mar. 2006a). Main themes of scientific work, In Biannual Report, Department of Microbiology (Max Planck Institute for Marine Biology), pp. 79-80.
Schüler, D. (Apr. 2004-Mar. 2006b). Survey of major projects, In Biannual Report, Research Concept (Max Planck Institute for Marine Biology ), pp. 13-14.
Schuler, D. (2004) Molecular analysis of a subcellular compartment: the magnetosome membrane in Magnetospirillum gryphiswaldense. Arch. Microbiol. 181, 1-7.
Schüler, D., and Frankel, R. (1999). Bacterial magnetosomes: microbiology, biomineralization and biotechnological applications. Appl Microbiol Biotechnol 52, 464-473.
Southward, C., and Surette, M. (2002). The dynamic microbe: green fluorescent protein brings bacteria to light. Mol Microbiol 45, 1191-1196.
Stephens, C. (2006) Bacterial cell biology: managing magnetosomes. Curr. Biol. 16, R363-R365.
Van Roessel, P., and Brand, A. (2002). Imaging into the future: visualizing gene expression and protein interactions with fluorescent proteins. Nat Cell Biol 4, E15-E20.
Walker, M., Quinn, T., Kirschvink, J., and Groot, C. (1988). Production of single-domain magnetite throughout life by sockeye salmon, Oncorhynchus nerka. J Exp Biol 140, 51-63.
Yamaoka, T. (2002). Regeneration therapy of pancreatic beta cells: towards a cure for diabetes? Biochem Biophys Res Comm 296, 1039-1043.
Blackwood, K., H. Kong, et al. (2006). In vivo evaluation of thymidine kinase over-expression to track canine bone marrow stromal cells using dual isotope SPECT. Fifth Annual Meeting of the Society for Molecular Imaging. Hawaii, Mol. Imaging. 5: 234.
Chambers, A.F., A.C. Groom, et al. (2002). "Dissemination and growth of cancer cells in metastatic sites." Nat. Rev. Cancer. 2: 563-572.
Goldhawk, D., C. McCreary, et al. (2006). Magnetic resonance imaging of cells overexpressing MagA, an iron transporter involved in magnetosome formation. Fifth Annual Meeting of the Society for Molecular Imaging. Hawaii, Mol Imaging. 5: 294.
Heyn, C., J. A. Ronald, et al. (2006). "In vivo MRI of cancer cell fate at the single-cell level in a mouse model of breast cancer metastasis to the brain." Magn. Reson. Med. 56: 1001-1010.
Jin, Y., H. Kong, et al. (2005). "Determining the minimum number of detectable cardiac-transplanted 111In-tropolone labelled bone-marrow-derived mesenchymal stem cells by SPECT." Phys. Med. Biol. 50: 4445-4455.
Jin, Y. H. Kong, et al. (2006). Cardiac transplanted 111In-tropolone-labelled autologous mesenchymal stem cells: in vivo radiotracer kinetics. Fifth Annual Meeting of the Society for Molecular Imaging. Hawaii, Mol. Imaging. 5: 403.
Komeili, A., Z. Li, et al. (2006). "Magnetosomes are cell membrane invaginations organized by the actin-like protein MamK." Science 311: 242-245.
Matsunaga, T., C. Nakamura, et al. (1992). "Gene transfer in magnetic bacteria: transposon mutagenesis and cloning of genomic DNA fragments required for magnetosome synthesis." J. Bacteriol. 174: 2748-2753.
Prato, F., D. Goldhawk, et al. (2006). Provisional patent U.S. Appl. No. 60/811784. U. S. P. Office. USA.
Stodilka, R., K. Blackwood, et al. (2006). Large animal hybrid SPECT/CT using a small field-of-view gamma camera: proof of principle for monitoring cardiac transplanted stem cells.
Fifth Annual Meeting of the Society for Molecular Imaging. Hawaii, Mol. Imaging. 5: 418.

(56) References Cited

OTHER PUBLICATIONS

Stodilka, R., K. Blackwood, et al. (2006). Performance of hybrid multi-spectral SPECT/CT in tracking transplanted cells in a canine model. Fifth Annual Meeting of the Society for Molecular Imaging. Hawaii, Mol. Imaging. 5: 407.

Tai, J.H., Nguyen, et al. (2006) Imaging pancreatic islet cell gene expression using dual-isotope SPECT/CT. Tenth Annual Meeting of the Canadian Diabetes Association. Toronto.

Pauser et al:"Liposome-encapsulated super-paramagnetic iron oxide particles as markers in an MRI-guided search for tumor-specific drug carriers" Anti-Cancer Drug Design. 1997, vol. 12, No. 2, pp. 125-135. ISSN:0266-9536. See whole document.

Hartung et al : "Labelling of macrophages using bacterial magnetosomes and their characterization by magnetic resonance imaging". In:Journal of Magnetism and Magnetic Materials, Proceedings of the sixth international conference on the scientific and clinical aplications of magnetic carriers, Krems (Austria), 17-120 May 2006. Edited by Use Hafeli and Wolfgang Schutt. Apr. 2007 (available online Dec. 13, 2006 (Dec. 13, 2006)), vol. 311, No. 1, pp. 454-459. ISSN: 0304-8853. See whole document.

Nakamura C et. "An iron-regulated gene, magA, encoding an iron transport protein of *Magnetospirillum* sp. strain AMB-1" The Journal of Biological Chemistry. Nov. 24, 1995 (Nov. 24, 1995), vol. 270, No. 47, pp. 28392-28396. ISSN:1083-351X. See especially abstract, lines 17-19; p. 28395, paragraph titled "Iron Transport in Membrane Visicles,", and figure 6.

Lang C et al: "Biogenic nanoparticles:production, characterization, and application of bacterial magnetosomes" J. Phys.:Condens. Matter. Sep. 2006, vol. 18, No. 38, pp. S2815-S2828. ISSN:0953-8984. See whole document.

Komeili A et al:"Moledular mechanisms of magnetosome formation" Annu. Rev. Biochem 207 (published online Mar. 19, 2007), vol. 76, pp. 351-366. ISSN:0066-4154. See whole document.

Schiller, D. (Apr. 2004-Mar. 2006b). Survey of major projects, In Biannual Report, Research Concept (Max Planck Institute for Marine Biology ), pp. 13-14.

\* cited by examiner

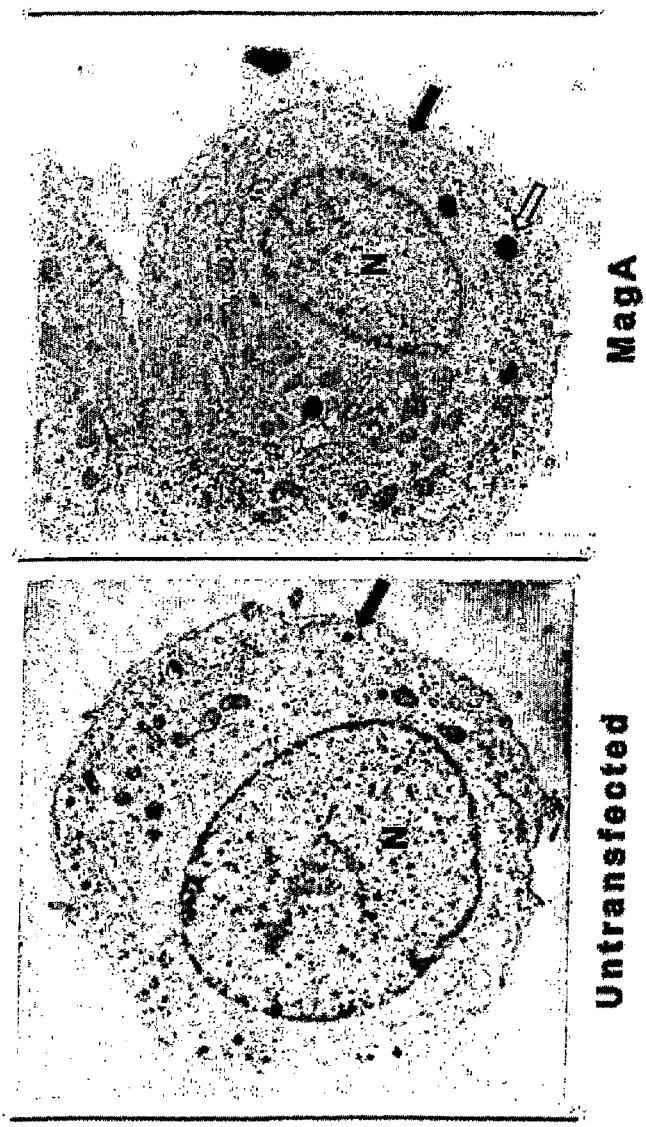

MAGNETOSOME GENE EXPRESSION IN EUKARYOTIC CELLS

The present application claims priority from U.S. Patent Application No. 60/811,784 filed Jun. 8, 2006 and U.S. Patent Application No. 60/879,791 filed Jan. 11, 2007.

FIELD OF INVENTION

The invention relates to the production of magnetosome-like structures in cells. More specifically, the invention provides in vitro and in vivo diagnostic and therapeutic methods using eukaryotic cells expressing magnetosome-like structures that act as contrast agents.

BACKGROUND OF THE INVENTION

Non-invasive mapping of cellular or subcellular events in living organisms, or molecular imaging, is an evolving and largely unexplored field. Magnetic resonance imaging (MRI) is used for in vivo cellular imaging and requires the use of cellular contrast agents. Many of the current developments in contrast agents have revolved around SPIO (super paramagnetic iron oxide) particles. These are specifically formed crystals of a mixture of ferrous and ferric oxides (magnetite). For MRI contrasting, these particles must be as small as possible and yet retain permanent magnetic properties (Bulte et al., 1994). Various companies have developed biologically compatible nanosphere and microsphere SPIO particles. These may be coated with a number of materials including protein, phospholipids, polysaccharide, dextran (Arbab et al., 2003) and silane polymer shells that may or may not further include targeting antibodies. However, they are not useful for long-term studies in which labelled cells divide and the SPIO contrast agent becomes diluted. In addition, SPIO particles alone cannot provide information on cellular and molecular function.

Gene expression systems are under development to couple protein expression with the formation of suitable contrast agents. Adenocarcinoma cells have been transfected with a ferritin gene cloned into a viral expression vector so that the cells will over-express heavy and light ferritin subunits (Genove et al., 2005). Upon culture in iron supplemented media, elevated cellular levels of ferritin provide a sufficient quantity of the crystalline ferrihydrite core for MRI.

Magnetosomes are endogeneous contrast agents that are membrane-bound structures produced by magnetotactic bacteria and contain magnetite or iron oxide mixtures (Bazylinski and Frankel, 2004). Due to their size specificity and distinctive crystal morphology, magnetosomes are good in vivo imaging contrast agents. The full complement of genes responsible for magnetosome synthesis in bacteria is still under investigation (Schüler, et al., 2006; Komeili et al., 2006; Grunberg et al., 2001). Reproducing the entire magnetosome structure in foreign cells has therefore not been accomplished. Current research and development has focussed on the isolation and characterization of the bacterial magnetosome particle (Schuler et al., Max Planck Institute for Marine Biology, Biannual Report, 2004-2006; Herborn et al., 2003).

U.S. Pat. No. 5,861,285 describes a method to make magnetic particles using transformed magnetic bacterium. U.S. Pat. No. 6,033,878 describes a fusion DNA sequence of a protein gene fused to a fragment of a magA gene coding for a protein bound to an organic membrane for covering magnetic particles produced in magnetic bacterium. U.S. Pat. No. 6,251,365 describes a magnetosome surrounded by a phospholipid membrane made by a formation process. U.S. patent application serial no. 2004/0048289 describes a protein specific to a magnetic particle membrane derived from a magnetic bacterium (*Magnetospirillum* sp.) AMB-1.

Magnetite has been reported in the tissue of numerous vertebrates; however, some mollusks and bacteria precipitate this iron mineral. It is the iron crystal that magnetotactic bacteria use to orient themselves in the earth's magnetic field. Crystalline magnetite has not been identified in mammals, nor has a definitive role been demonstrated for magnetosome-like structures in migratory birds. Hence, the role of magnetosomes in vertebrates, including mammals, is still speculative (Kirschvink et al., 2001).

An iron regulated gene, magA, which encodes a membrane-bound, iron-transport protein involved in magnetite synthesis has been identified in *Magnetospirillum* species of bacteria (Bazylinski and Frankel, 2004; Matsunaga et al., 1992; U.S. Pat. No. 6,033,878).

While the prior art has demonstrated that magnetic particles as contrast agents can be made in prokaryotic systems, there still remains a need to develop a method for developing contrast agents in eukaryotic cells for a variety of clinical diagnostic and therapeutic applications.

SUMMARY OF THE INVENTION

The present invention is directed to cells that produce magnetosome-like structures, methods for making such cells and methods for using such cells in a variety of diagnostic and therapeutic methods in vivo, in vitro and ex vivo. For example the invention permits long-term in vivo MRI with enhanced contrast to follow the localization, proliferation and differentiation of transfected cells in tissues and organs as well as image sub-cellular structures in both prokaryotes and eukaryotes. The in vivo tracking of cells, including progenitor cells such as stem cells that differentiate into mature cells with highly specific functions, is a valuable research and clinical tool.

The invention provides constructs comprising one or more magnetosome protein nucleic acid sequences in a vector with suitable inducible promoters. Such constructs can further comprise other genes as desired.

According to an aspect of the present invention is a magnetosome-like structure, said structure being a contrast agent. In aspects, this contrast agent can be used in vitro, in vivo and ex vivo.

According to an aspect of the present invention is a magnetosome-like structure, said structure being isolated from a eukaryotic cell and being a contrast agent for use in MRI.

According to an aspect of the present invention is an eukaryotic cell comprising a magnetosome-like structure that acts as a contrast agent.

According to another aspect of the present invention is an eukaryotic cell comprising an expressible nucleic acid construct, said construct comprising one or more magnetosome protein nucleic acid sequences operatively linked to a promoter.

According to another aspect of the present invention is a cell transfected with a construct comprising a gene selected from a magnetosome gene and/or a magnetosome-associated gene.

According to an aspect of the present invention is a method for making a cell that expresses a magnetosome-like structure as a contrast agent, the method comprising;

transfecting a cell with a construct comprising one or more magnetosome genes under the control of an inducible promoter.

In aspects of the invention, the magnetosome-like structure may be further isolated from the cell.

According to another aspect of the present invention is a method for making a contrast agent in an eukaryotic cell or a non-magnetic prokaryotic cell, said method comprising;

transfecting said cell with a construct comprising one or more magnetosome genes under the control of a promoter.

According to another aspect of the present invention is an ex vivo method for genetically altering stem cells to produce a contrast agent, said method comprising the steps of: maintaining a plurality of undifferentiated embryonic stem cells in vitro in a culture medium said undifferentiated, embryonic stem cells comprising: a mammalian embryonic stem cell which (i) remains uncommitted and undifferentiated while passed in vitro, (ii) is implantable in vivo at a chosen anatomic site as an uncommitted cell, and (iii) engrafts in situ after implantation in a mammal at a local anatomic site, and, (iv) contains a vector comprising a DNA sequence operably linked to a promoter, wherein the DNA sequence encodes a magnetosome protein; and subsequently culturing said embryonic stem cells for a predetermined time in a culture media to yield a cellular inoculum comprising cells in which differentiation has been initiated.

In aspects of the invention, the cellular inoculum is administered to a recipient to a desired location and can be subjected to MRI to track the differentiation of the stem cells in vivo.

According to a further aspect of the present invention is a method for genetically altering undifferentiated stem cells so that they contain a magnetosome-like structure comprising a dense core vesicle that acts as a contrast agent, said method comprising;

transfecting said stem cell with a nucleic acid sequence encoding one or more magnetosome proteins under the control of a suitable promoter.

According to another aspect of the present invention is the use of a cell containing a magnetosome-like structure in a diagnostic or therapeutic method to locate and/or track the cell in vitro or in vivo.

According to another aspect of the present invention is eukaryotic cell comprising a recombinant magnetosome-like structure.

According to a further aspect of the present invention is a transformed eukaryotic host cell comprising a plasmid expressing one or magnetosome genes. In aspects of the invention the host cell can be a non-magnetic prokaryotic cell.

Other features and advantages of the present invention will become apparent from the following detailed description. It should be understood, however, that the detailed description and the specific examples while indicating embodiments of the invention are given by way of illustration only, since various changes and modifications within the spirit and scope of the invention will become apparent to those skilled in the art from the detailed description.

BRIEF DESCRIPTION OF THE DRAWINGS

The present invention will become more fully understood from the detailed description given herein and from the accompanying drawings, which are given by way of illustration only and do not limit the intended scope of the invention.

Magnetosome gene expression in eukaryotic cells was carried out using standard transfection procedures. The production of dense core vesicles used magnetosome genes and the cell's endogenous machinery to amplify magnetite formation.

Figure 1A:
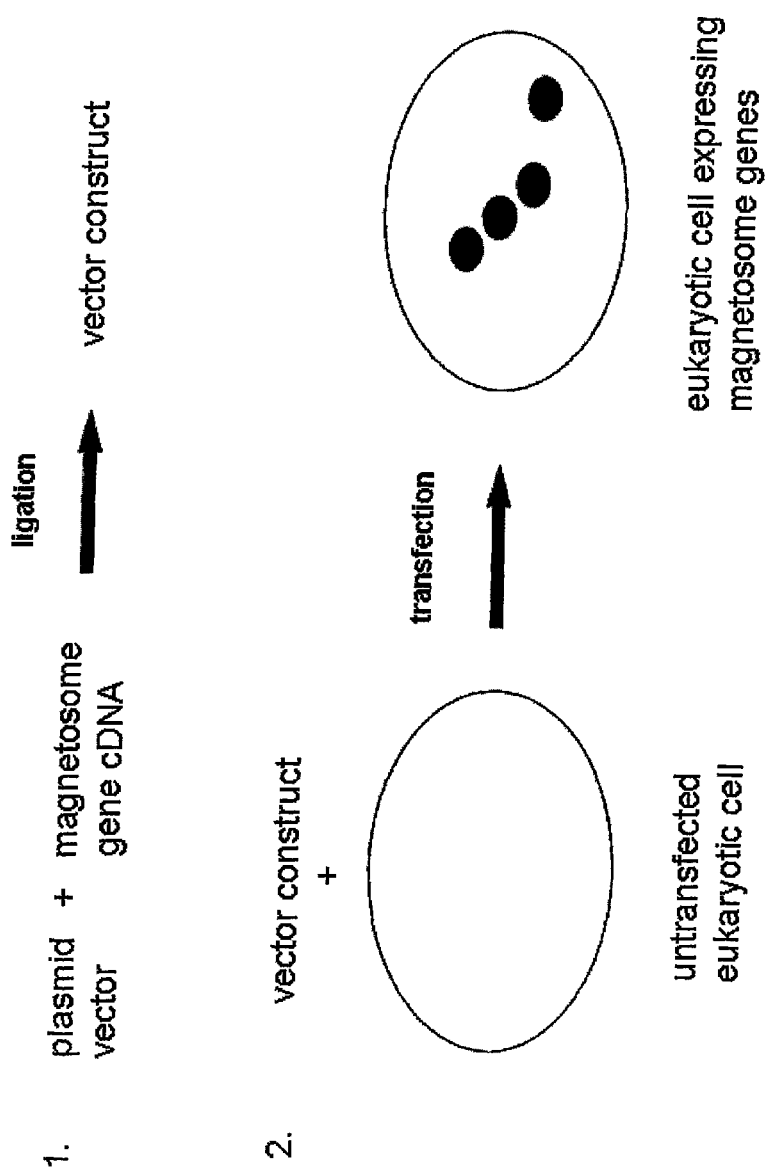
FIG. 1A shows the transfection of eukaryotic cells with magnetosome gene(s).
Figure 1B:
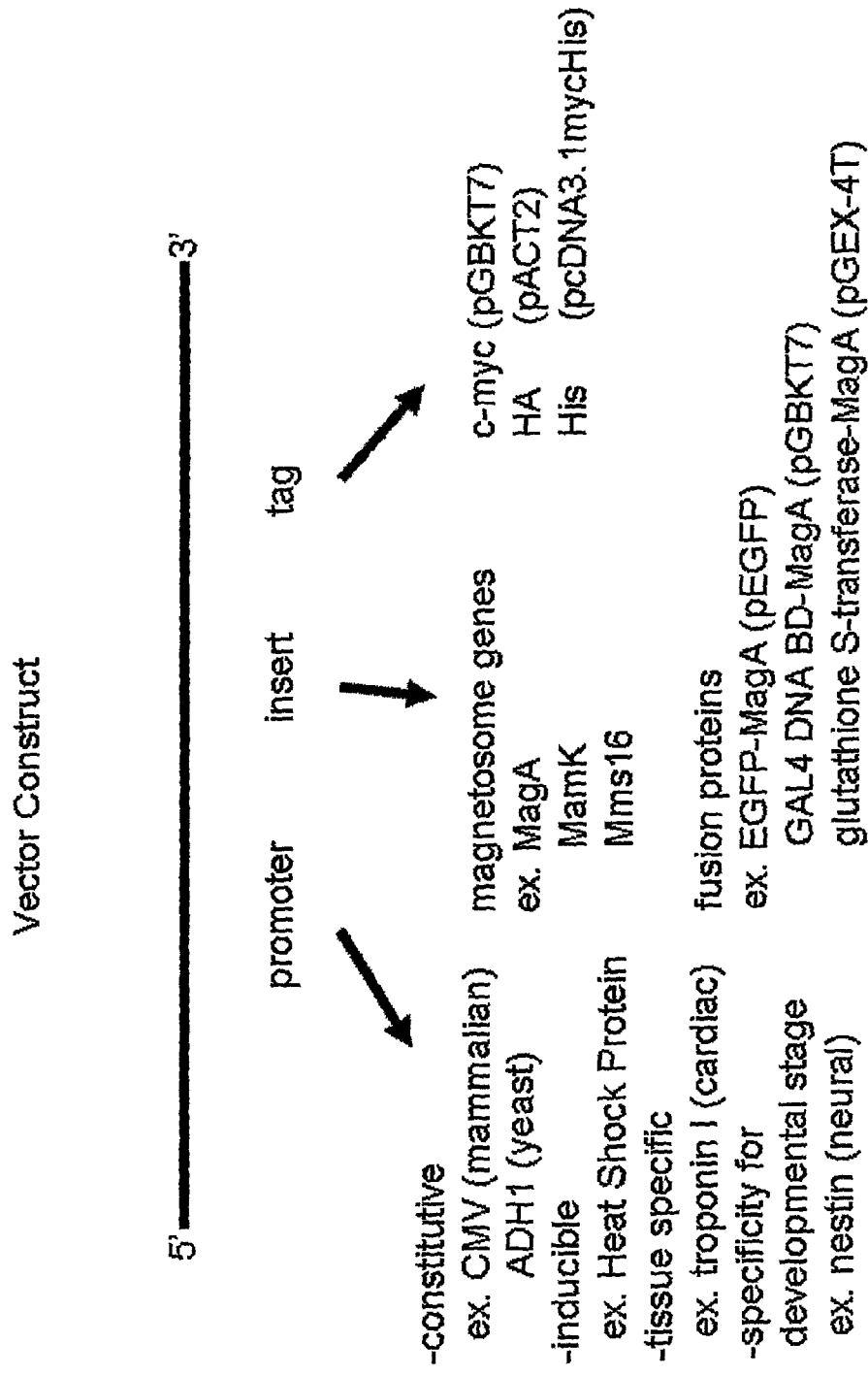

FIG. 1B shows the vector constructs. Eukaryotic expression vectors were designed with promoter sequences and magnetosome cDNA insert. Overexpressed protein was tagged by fusion with marker proteins, such as EGFP, or small peptide epitopes, such as c-myc, hemaglutinin (HA), or polyhistidine (His).

Figure 2A:
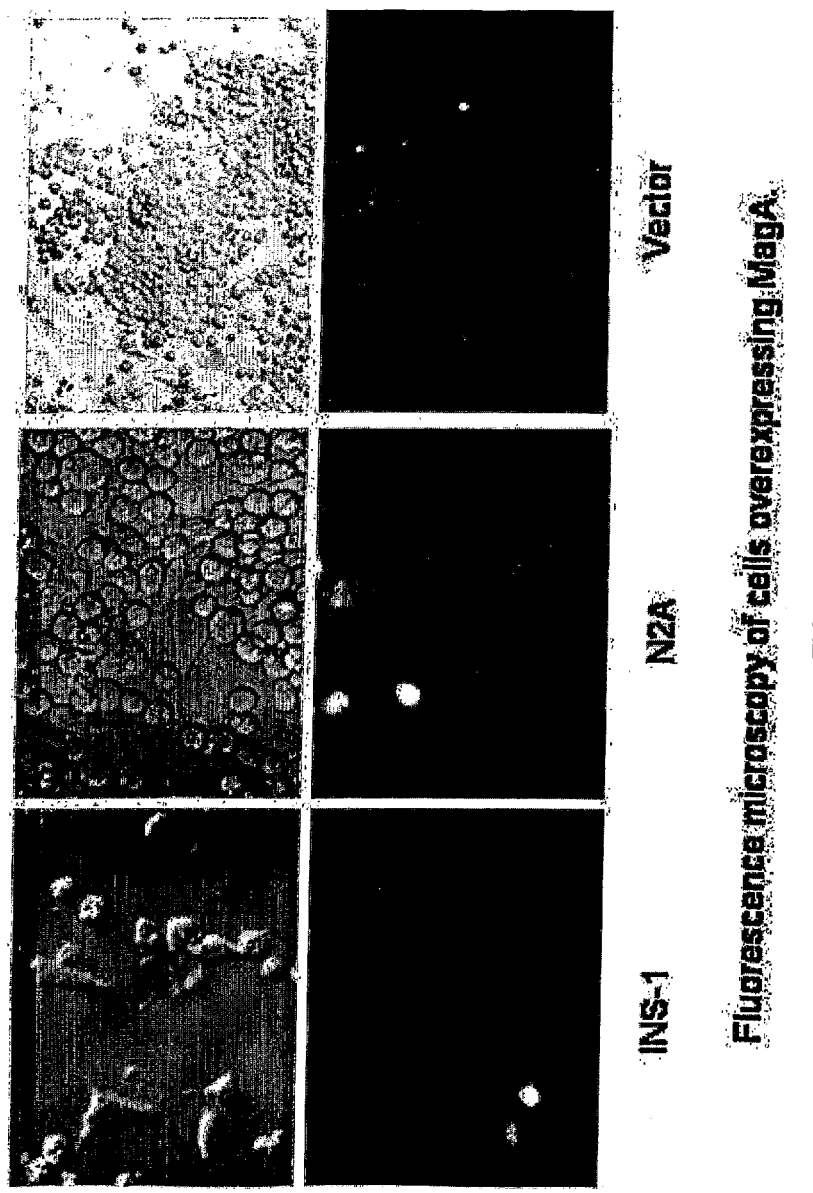

FIG. 2A shows fluorescence microscopy of cells overexpressing MagA. The fluorescence micrographs show INS-1 and N2A cells transfected with MagA in pEGFP. The vector control is depicted in N2A cells. Bright field images show cells under Hoffman Modulation Contrast optics. Cells expressing MagA are ×400. The vector control is ×100.

Figure 2B:
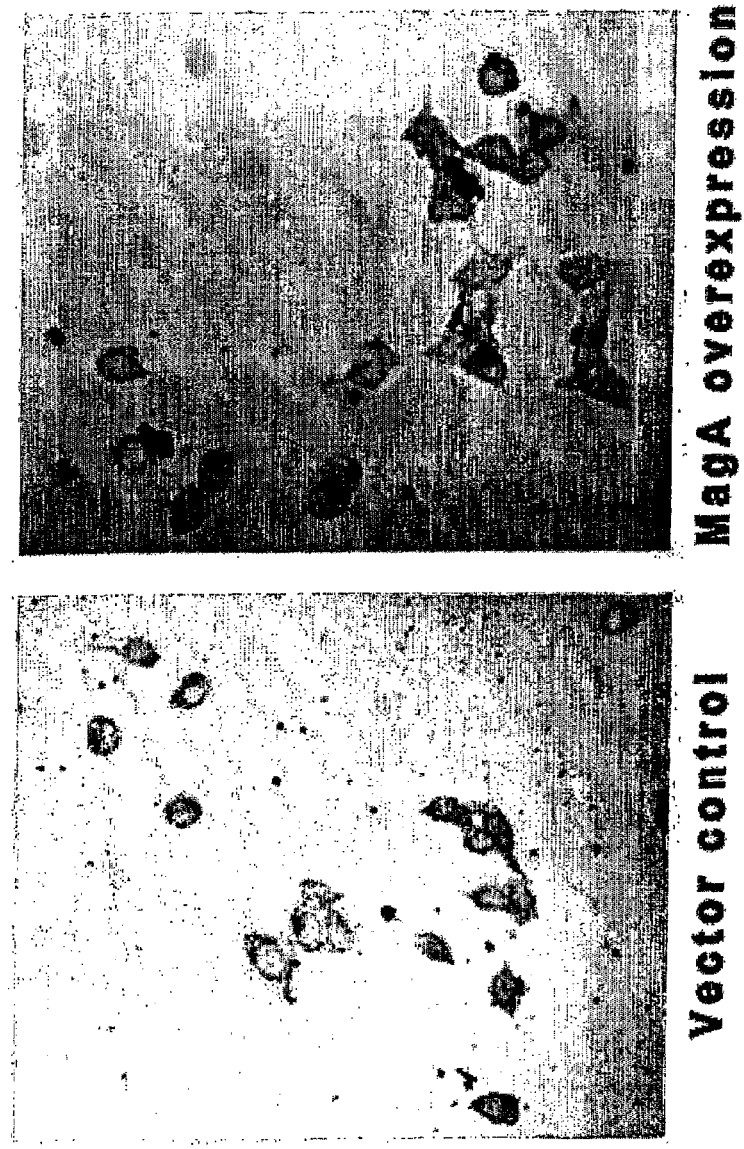

FIG. 2B shows prussian blue staining of INS-1 cells. Beta cells were transfected with pEGFP, with and without a MagA cDNA insert. Following transfection, cells were cultured in media supplemented with 250 μM ferric nitrate. Prussian blue staining of transfected cells indicates the degree of iron loading.

Figure 2D:
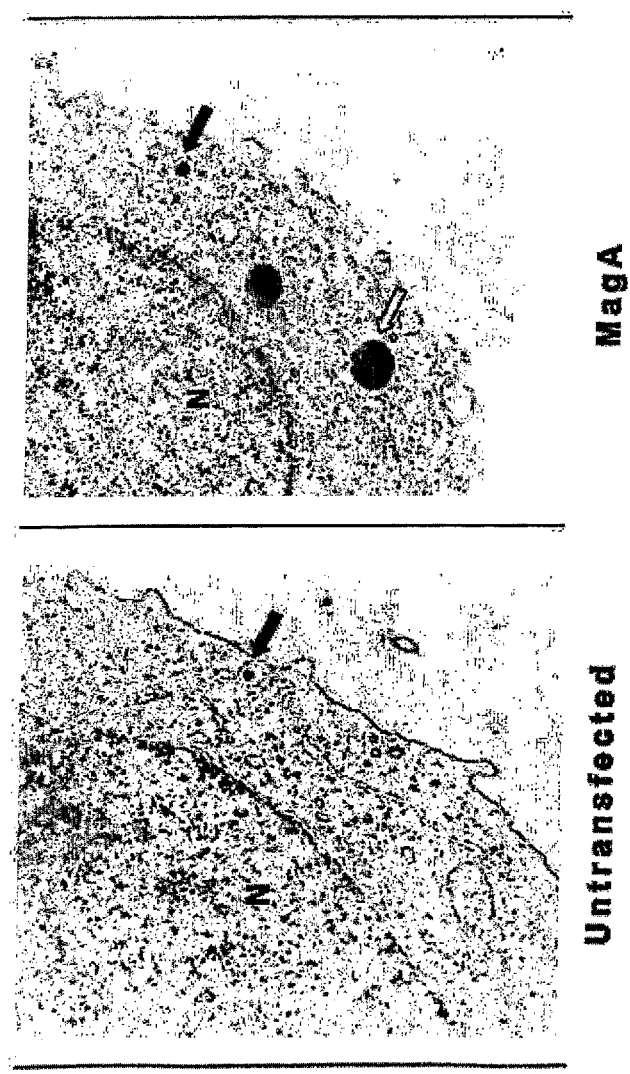

FIG. 2C, 2D show scanning electron micrographs of INS-1 cells. The electron micrographs of beta cells show differences in subcellular morphology depending on the expression of EGFP-MagA. The untransfected sample exhibits typical islet cell structure, including insulin secreting vesicles (filled arrows). MagA expressing cells show additional dense core vesicles (open arrow) that are distinct from insulin secretory vesicles and not detected in untransfected cells. Magnification is approximately ×18,000 (C) and ×40,000 (D). N, nucleus.

Figure 2E:
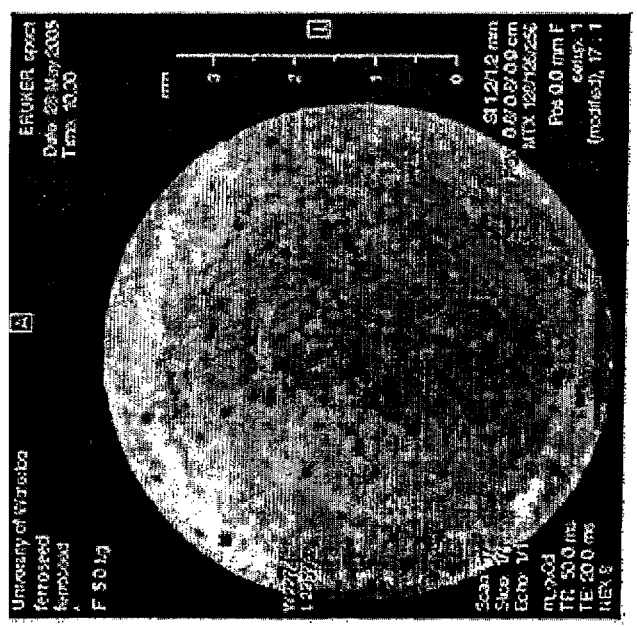

FIG. 2E shows MR imaging of INS-1 cells transfected with MagA. Transfected cells were examined by MRI using a simple Gradient Echo with a TE of 20 ms and showed some areas of signal loss.

Figure 3:
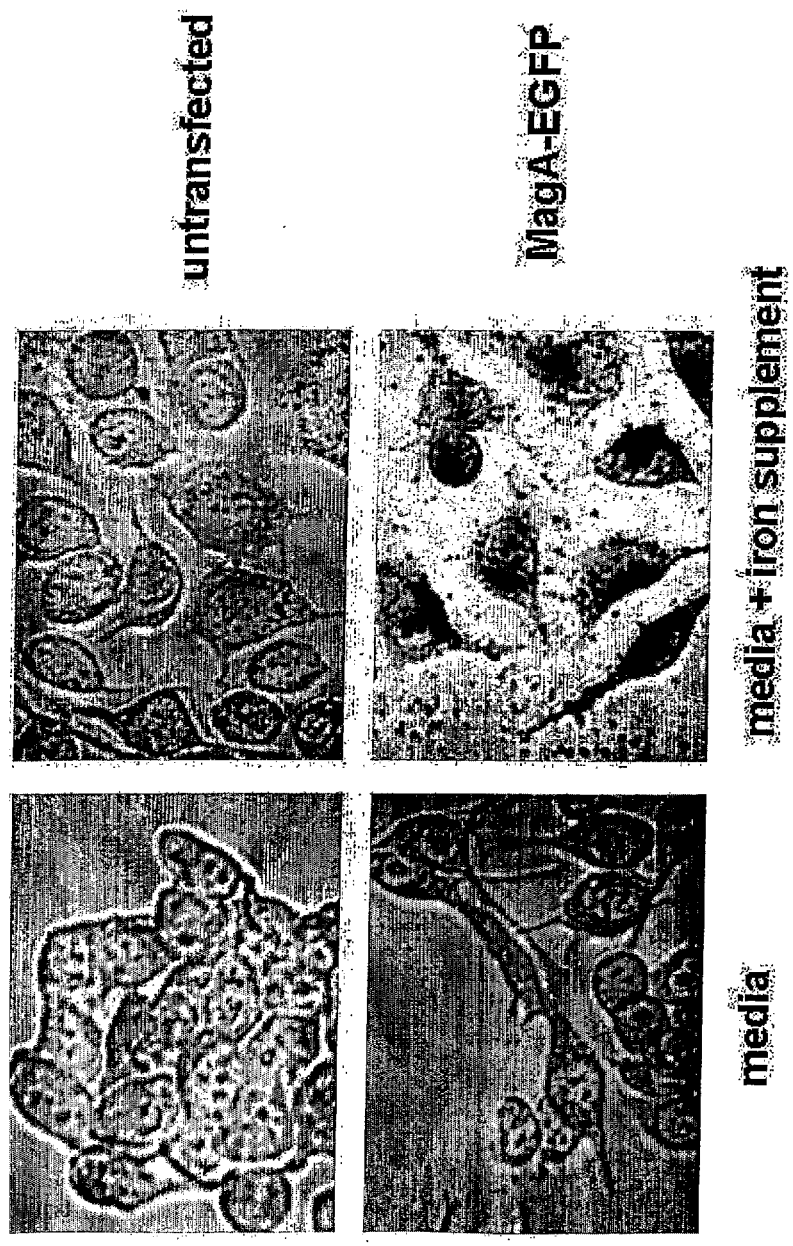

FIG. 3 shows Prussian blue staining of N2A cells transfected with MagA-EGFP where the culture media was supplemented with ferric nitrate.

Figure 4:
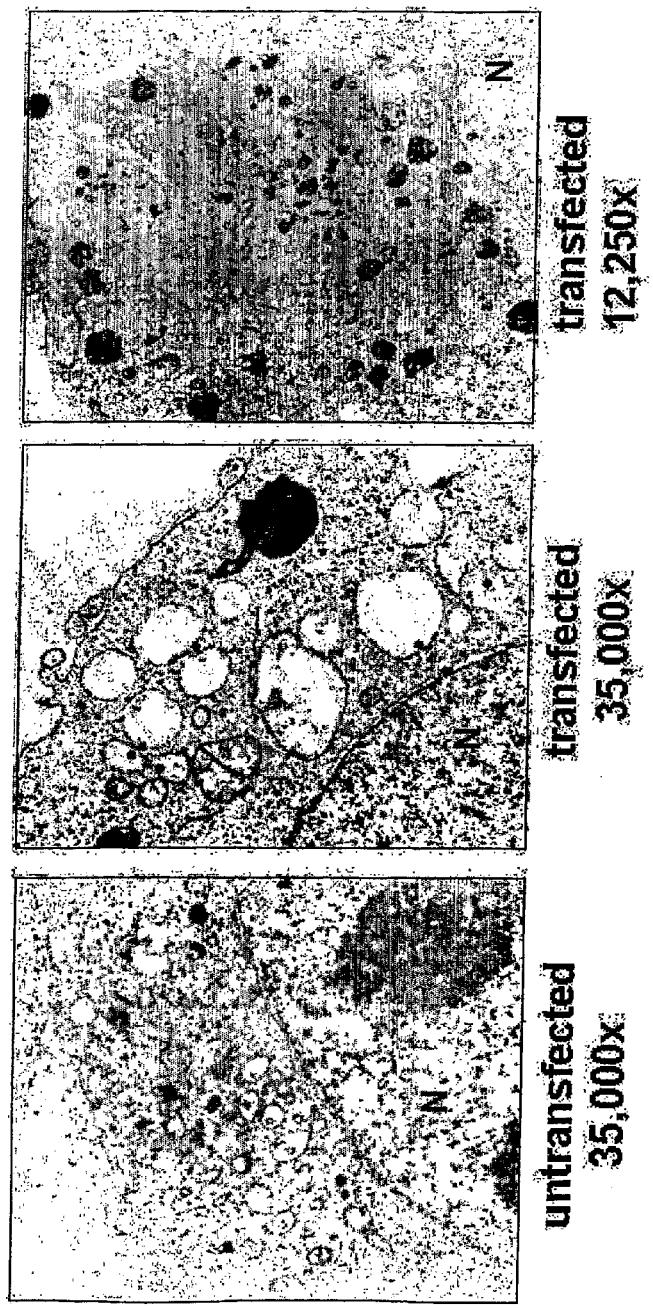

FIG. 4 shows the ultrastructure of MagA-EGFP overexpressing N2A cells by transmission electron microscopy. N=nucleus.

Figure 5:
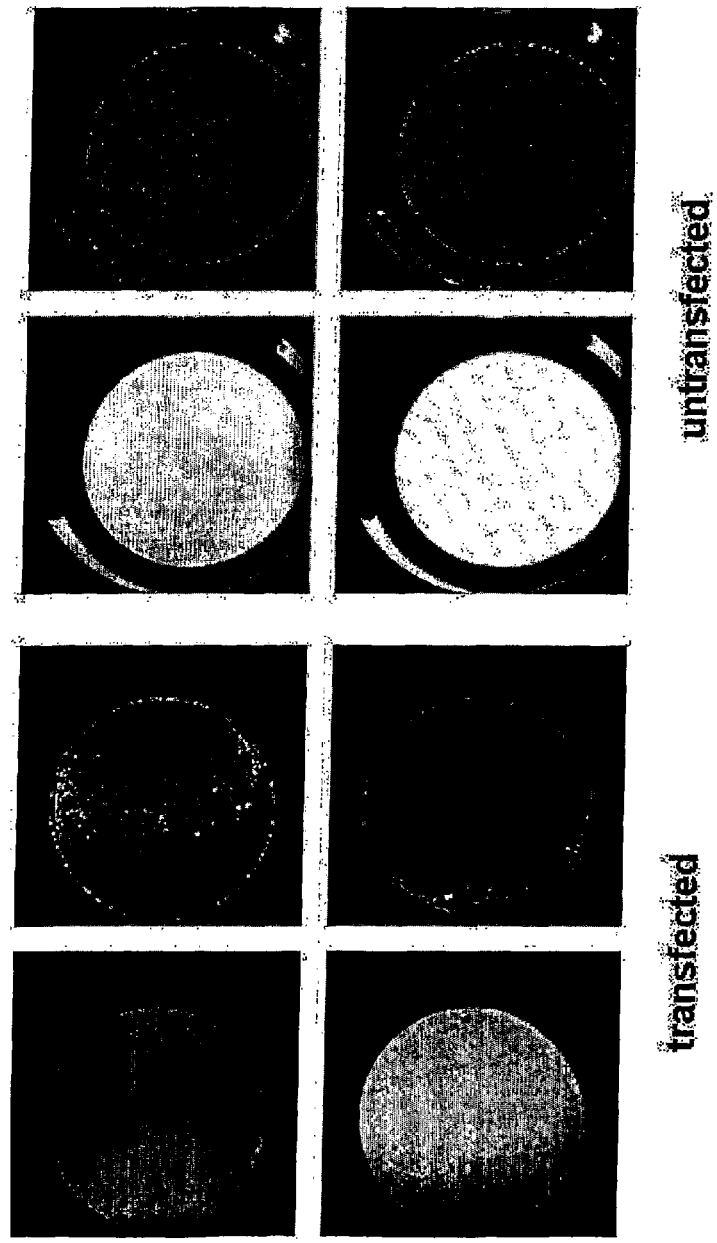

FIG. 5 shows MR imaging of N2A cells expressing MagA.

Figure 6:
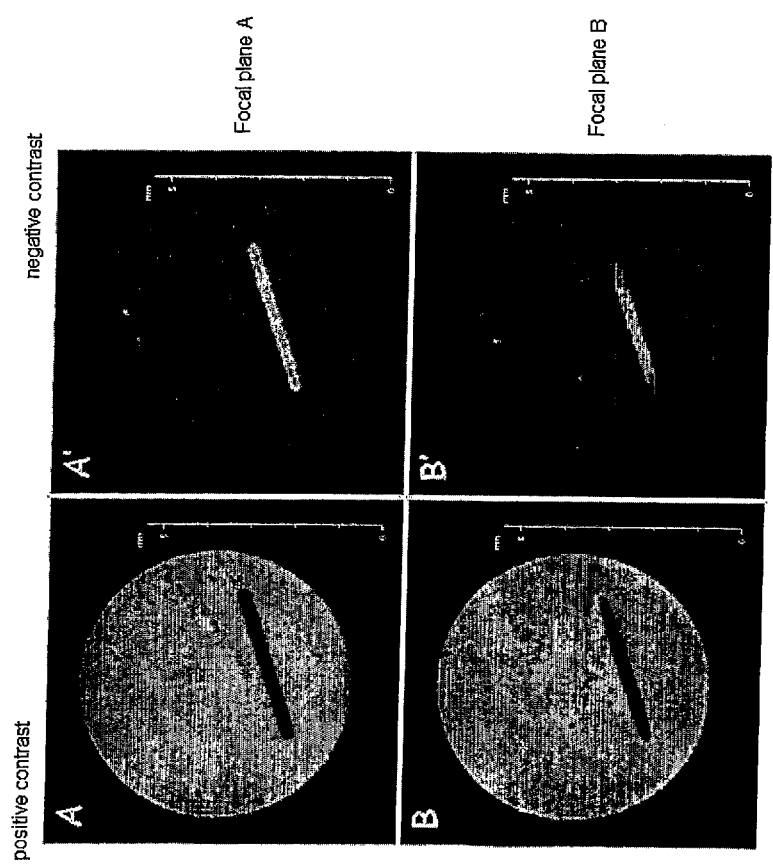

FIG. 6 shows a further example of MR imaging of N2A cells expressing MagA. Positive (A,B) and negative (A',B') images show areas of signal loss in two adjacent planes of focus. A and A' are both from one plane of focus, while both B and B' are a second plane of focus. A human hair marks the plane of focus. The image resolution is 65×65×125 cubic micrometer.

Figure 7A:
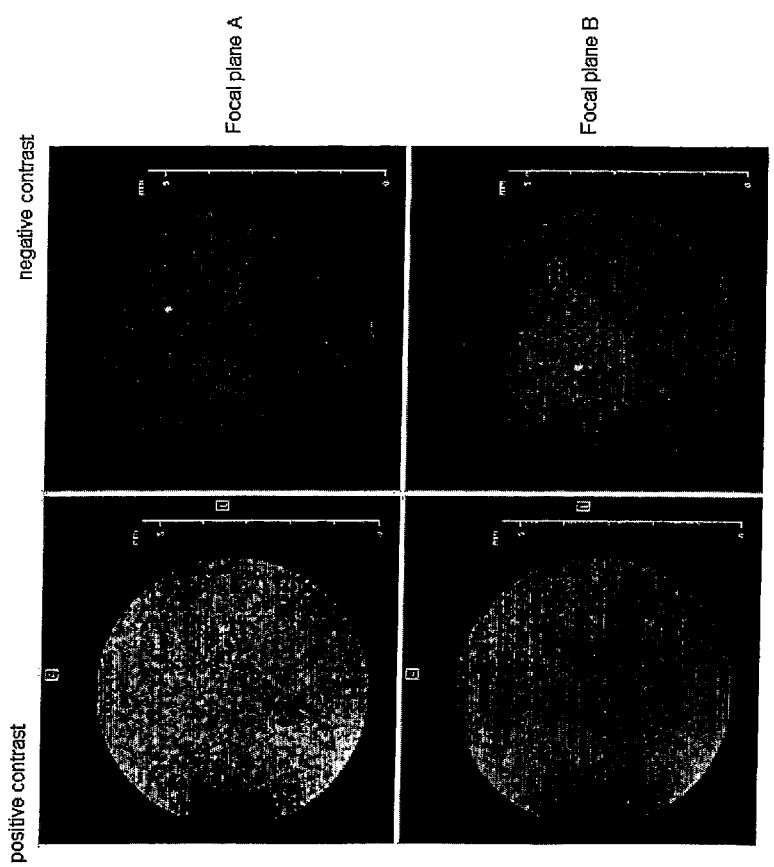
Figure 7B:
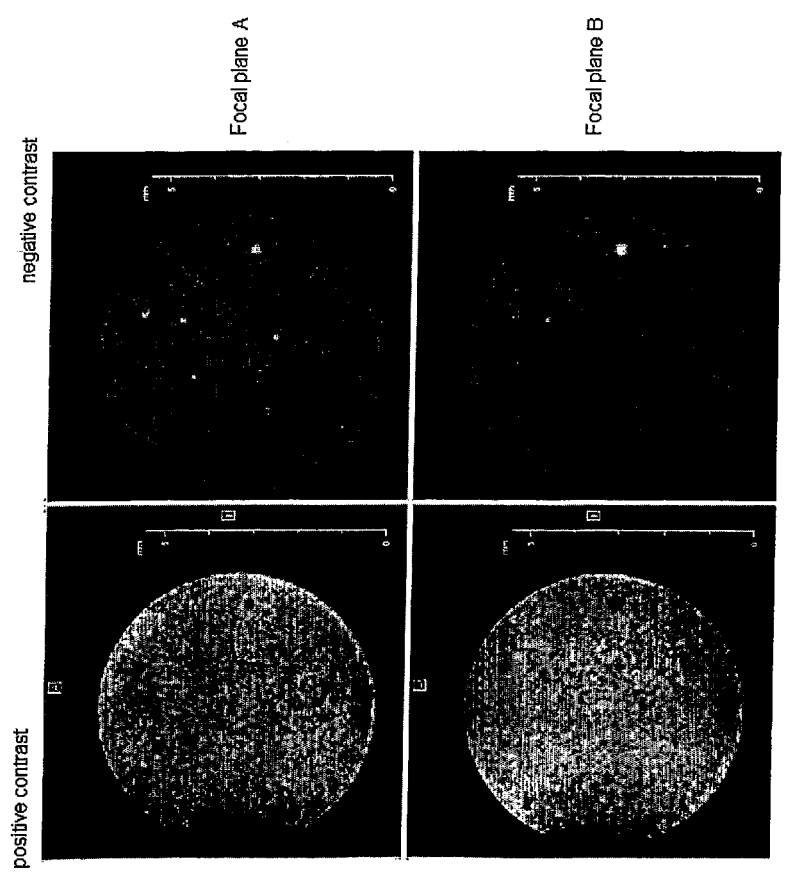
Figure 7C:
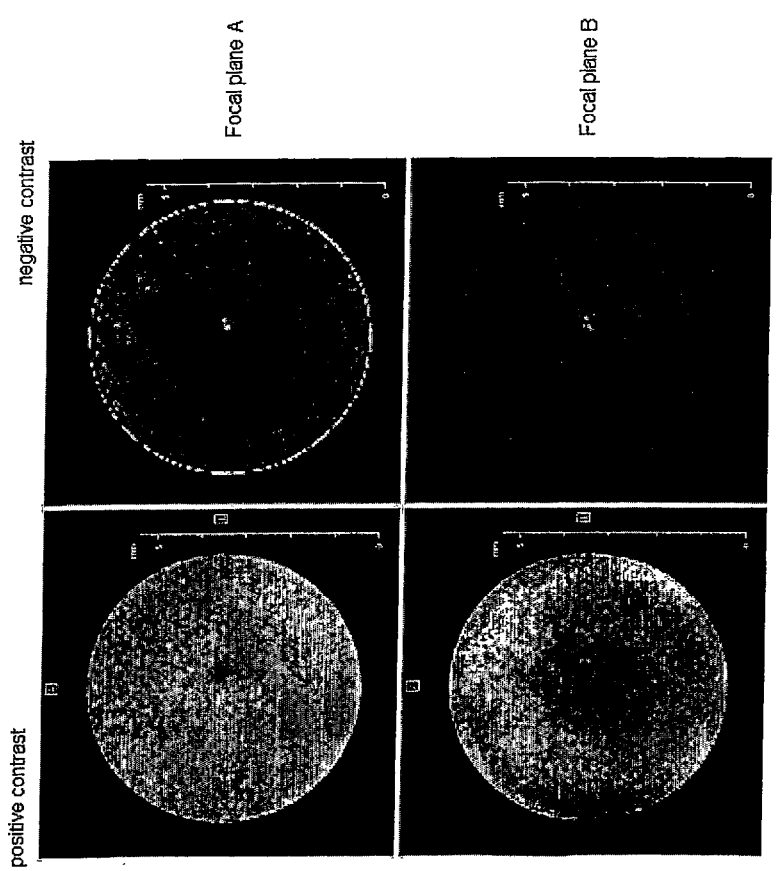
Figure 7D:
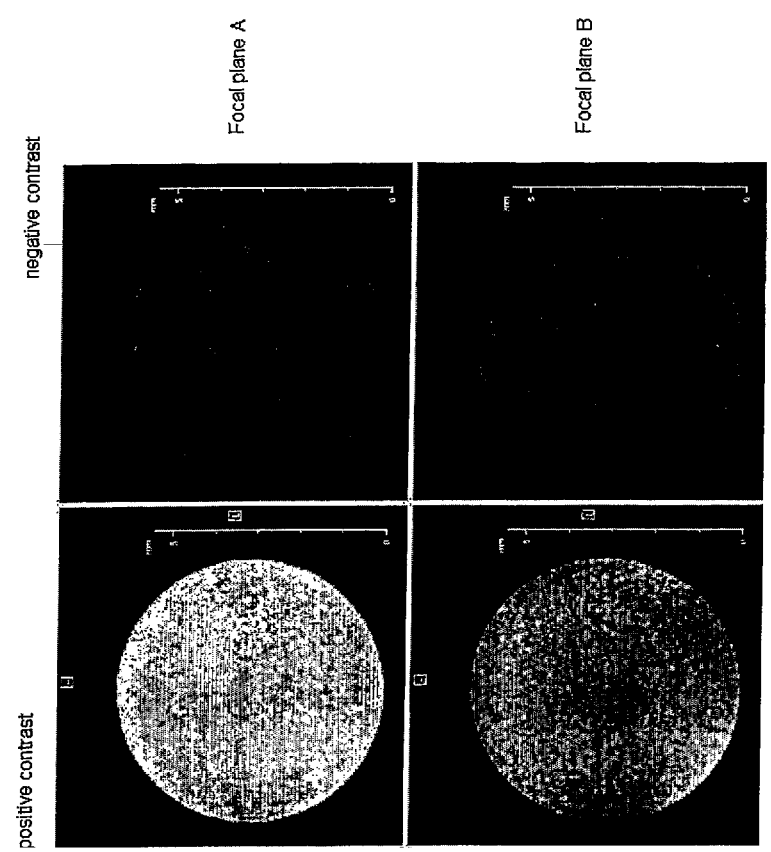
Figure 7E:
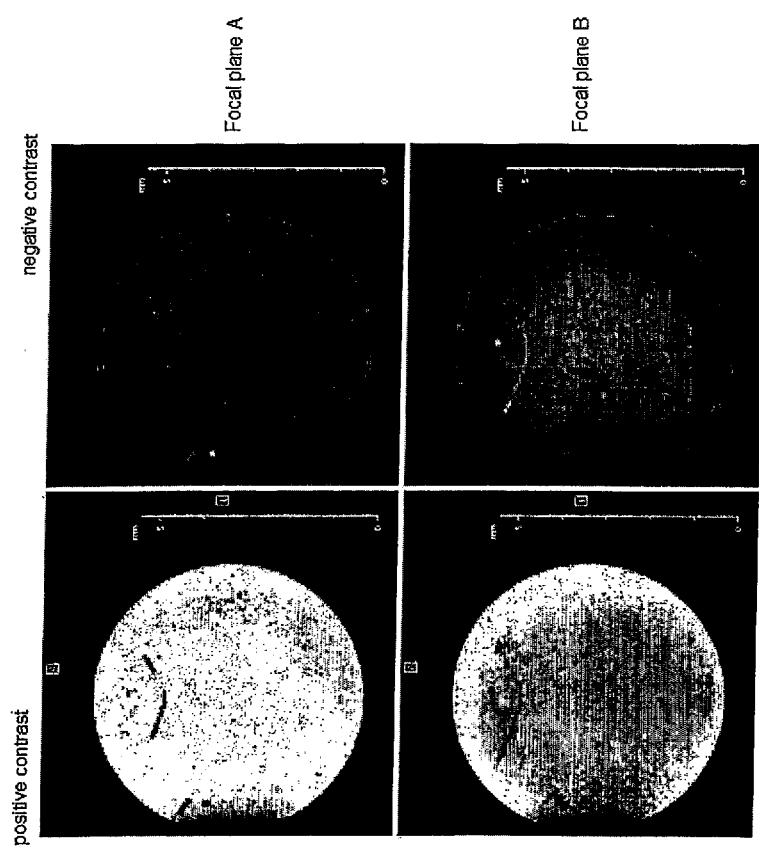
Figure 7F:
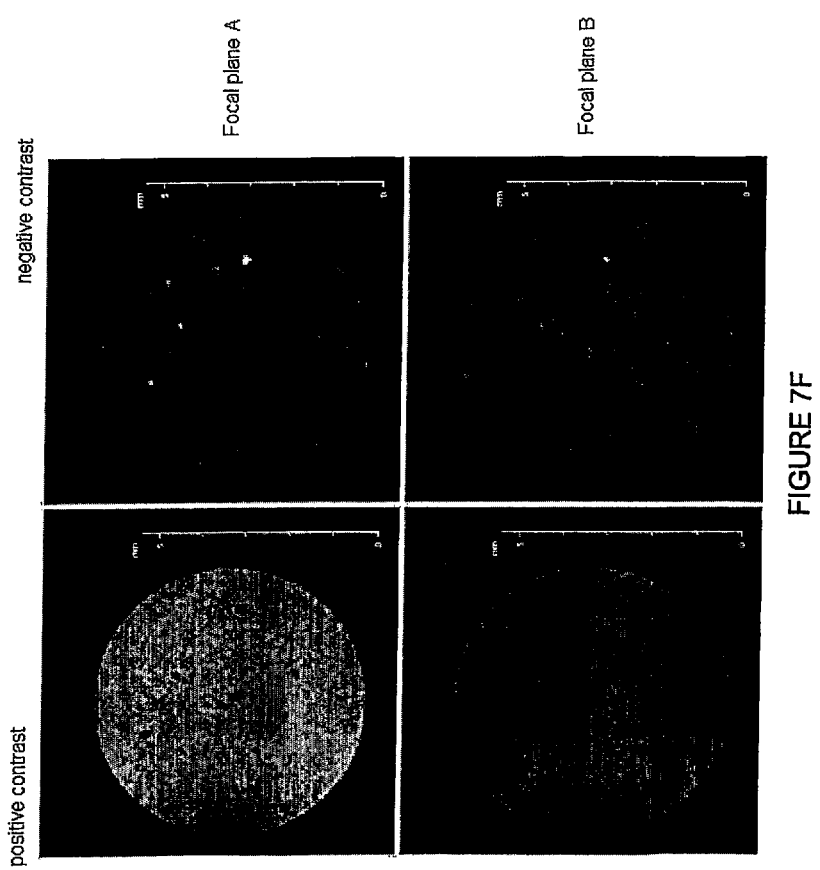
Figure 7G:
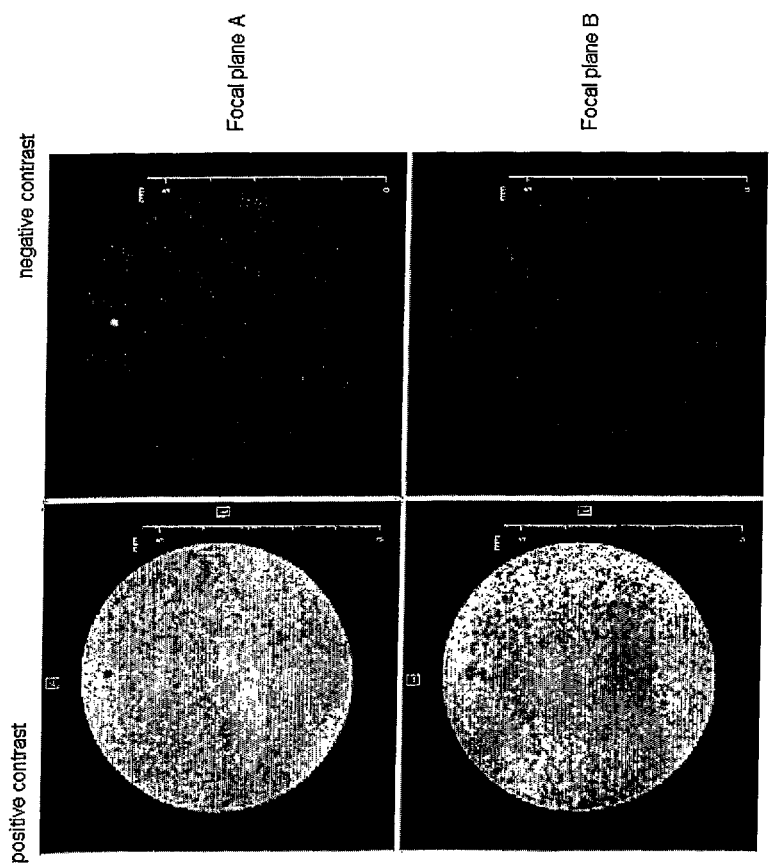
Figure 7H:
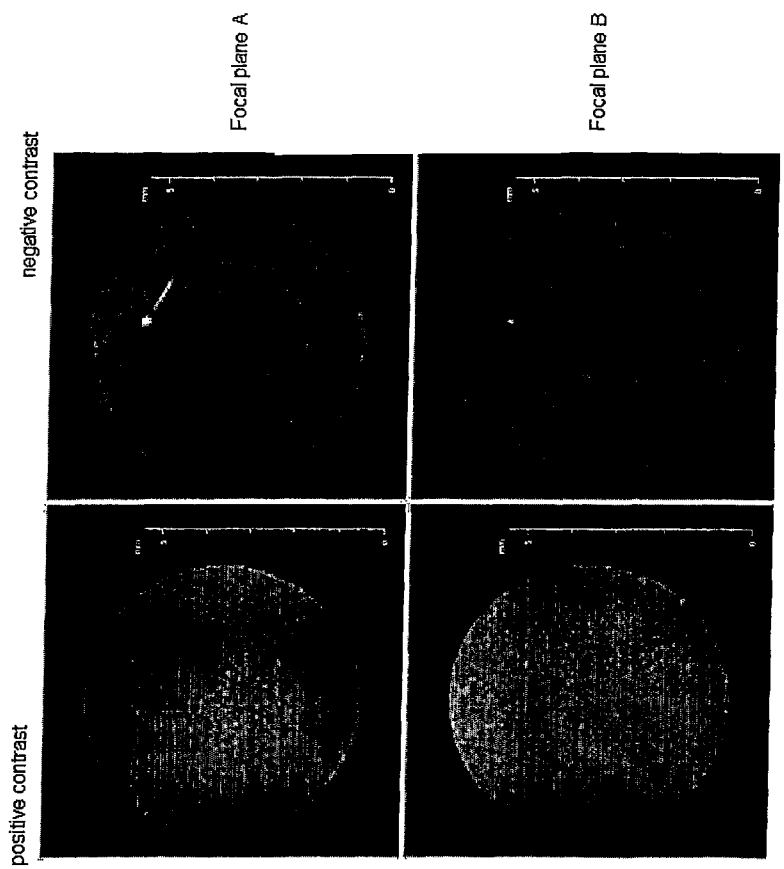

FIGS. 7A-7H show yet further examples of MR imaging of N2A cells expressing MagA. Positive and negative images are shown for two adjacent planes of focus. In FIGS. 7E and 7H a human hair marks the plane of focus.

Figure 8A:
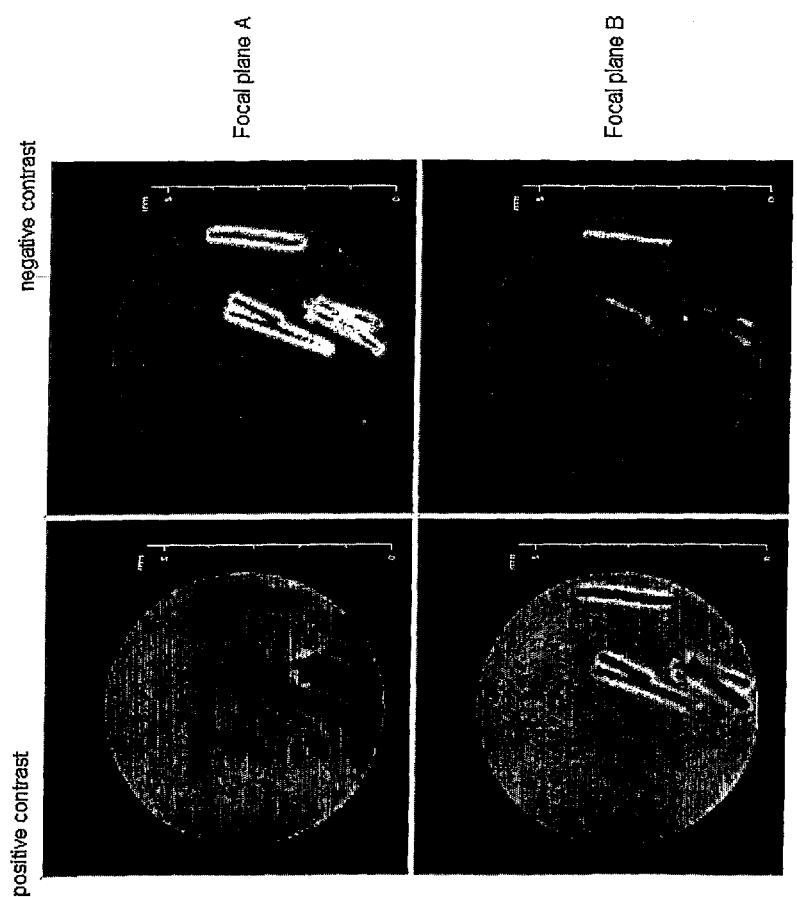
Figure 8B:
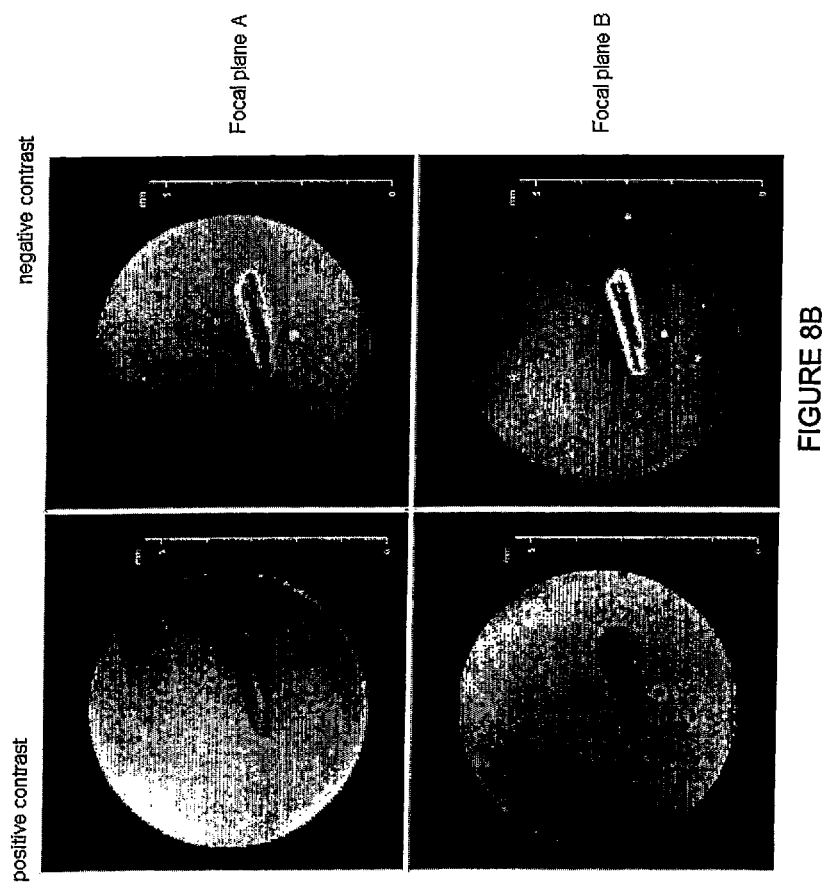
Figure 8C:
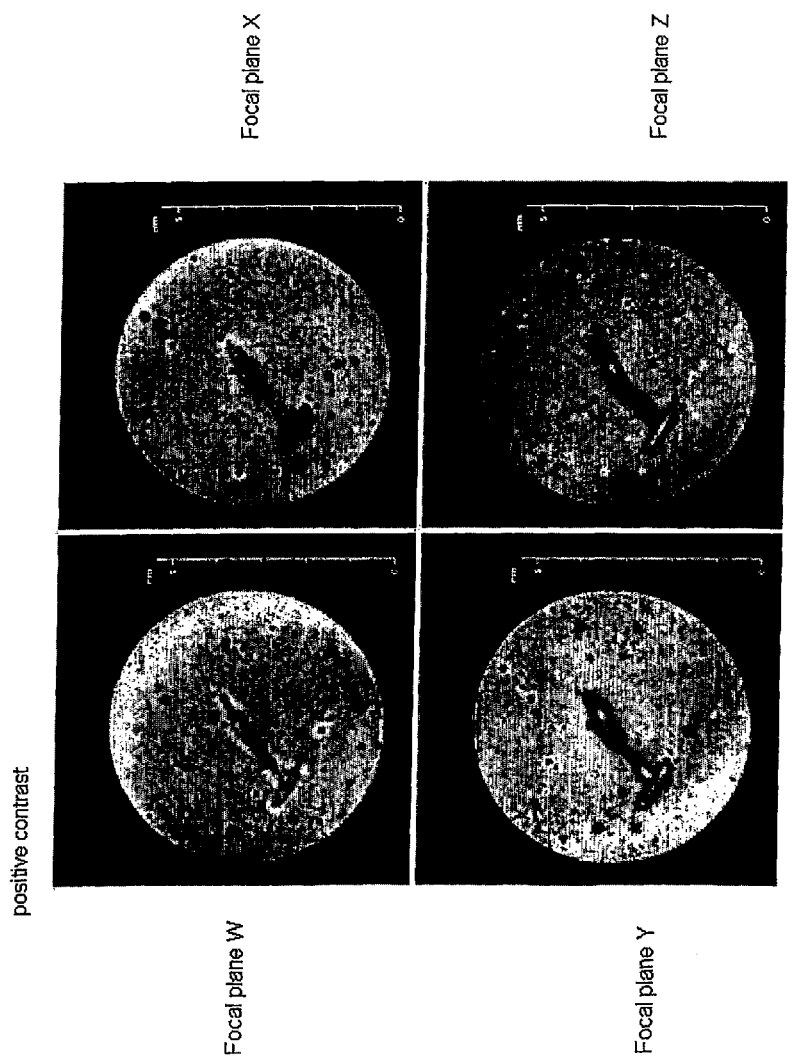
Figure 8D:
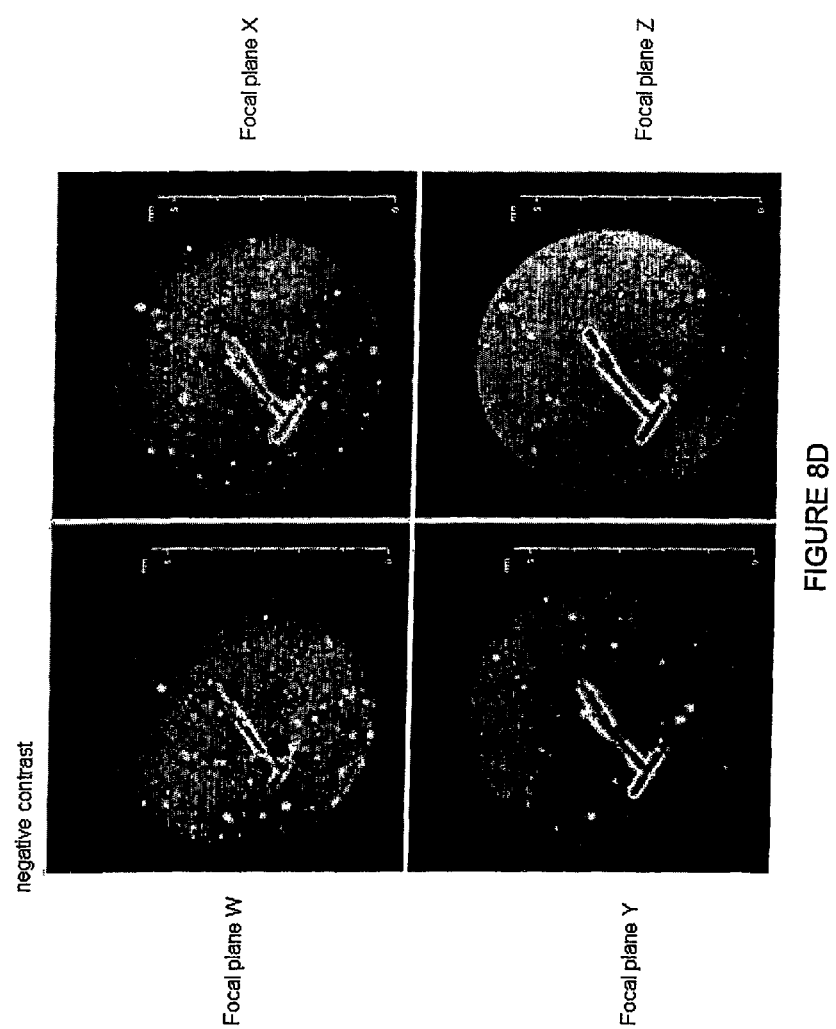
Figure 8E:
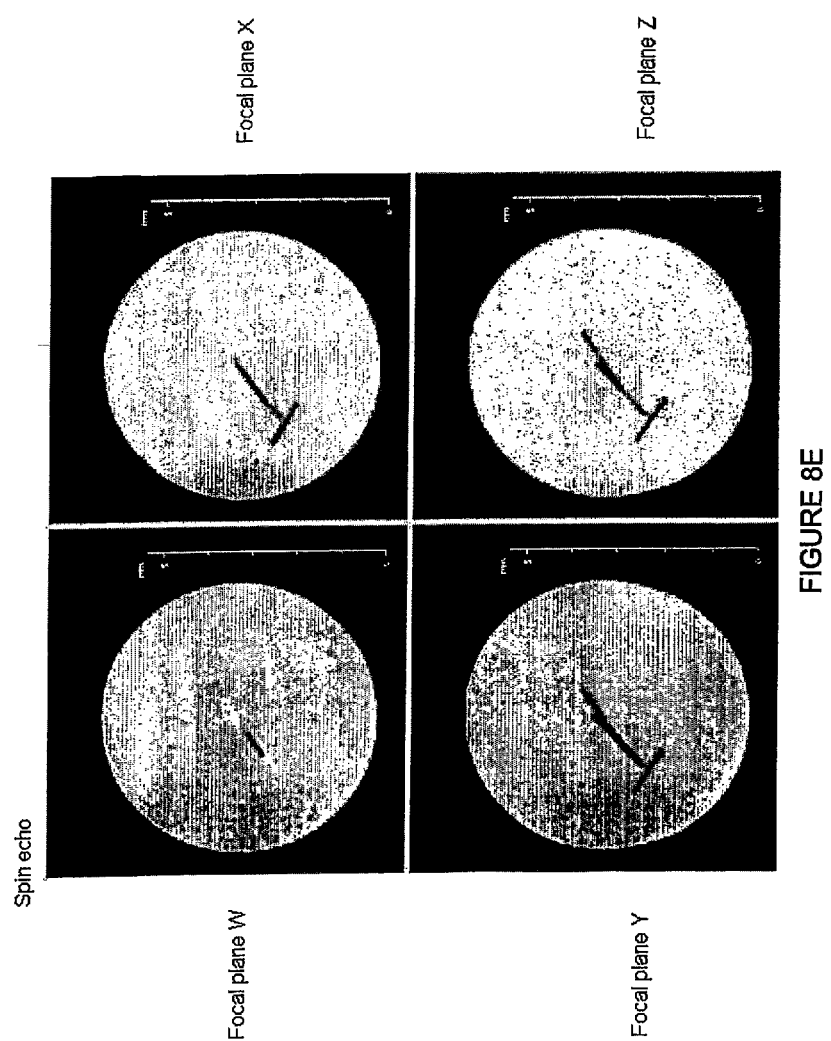

FIGS. 8A-8E show different images pertaining to still a further MagA expression demonstration. FIG. 8A shows MR imaging of a gelatin mold alone in the absence of cells, in positive and negative contrast images, at 2 different focal planes. FIG. 8B shows the background provided by 1 million cells expressing vector alone without MagA, in positive and negative contrast images, at 2 different focal planes. FIGS. 8C, 8D, and 8E pertain to cells comprising a vector with MagA insert. FIGS. 8C and 8D each show 4 different focal planes (W, X, Y, Z) in positive contrast and negative contrast images, respectively, while FIG. 8E shows spin echo imaging at these 4 focal planes. Spin echo imaging sequences at each focal plane indicate that signal voids cannot be attributed to air pockets. Human hair marks the focal plane.

DETAILED DESCRIPTION OF THE
PREFERRED EMBODIMENTS

An aspect of the invention provides genetically engineered cells that produce magnetosome-like structures as contrast agents for mapping and/or imaging of organs, tissues, cells, sub-cellular structures, proteins and peptides in living organisms both in vivo and in vitro. The method of the invention genetically alters cells to produce magnetosome-like structures as large dense core vesicles that form MR contrast agents in the cell. Certain aspects of the invention also provide magnetosome gene constructs that may be expressed from vectors bearing inducible promoters or encoding other useful genes for targeting cells or for therapeutic treatments that can be followed by functional imaging or long-term tracking of transfected cells. As such, various cell processes, for example, cellular migration, proliferation, differentiation and apoptosis can be tracked using the present invention.

Magnetosome-like structures typically comprise iron-containing particles enclosed within membrane vesicles. In naturally-occurring instances in bacteria, magnetosomes have been shown to contain crystalline particles of magnetite ($Fe_3O_4$) or greigite ($Fe_3S_4$). Most magnetotactic bacteria produce crystals of magnetite. Characterization of iron-containing particles that are incorporated into magnetosomes are discussed in several articles; for example, Stephens (2006) and Schuler (2004). Without wishing to be bound by theory, while the mechanism of magnetite biomineralization is not completely understood (Schuler, 2004), it is proposed to involve the uptake of ferric ion ($Fe3+$). This is also the species of iron bound by the transferrin receptor in mammalian cells.

A beneficial feature of the present invention is the fact that the genetically altered cells of the invention can continue to express magnetosome genes and produce magnetosome-like structures in vivo during growth, differentiation and/or replication of the cell. As a result such cells can be visually tracked as they grow, differentiate and/or replicate inside a host while maintaining detectable levels of magnetosome-like structures, and in certain examples without dilution of the magnetosome-like structure. Therefore, these structures may provide long-term in vivo contrast agents in a wide variety of cells, tissues, organs, etc.

In aspects of the invention the cells are non-magnetic prokaryotic cells or any type of eukaryotic cell capable of expressing a bacterial magnetosome gene. Any type of mammalian cell is suitable for use in the present invention for production of a magnetosome-like structure. For example, any human cell type that is useful for diagnostic, therapeutic or research purposes may be modified to express magnetosome gene(s) and produce magnetosome-like structures. Non-limiting examples of human cells that have been used for research purposes are MCF-7 (breast cancer), MDA-MB-438 (breast cancer), U87 (glioblastoma), A172 (glioma), HeLa (cervical cancer), HL60 (promyelocytic leukemia), A549 (lung cancer), HEK 293 cells (kidney), SHSY5Y (neuroblastoma cells, cloned from a myeloma), Jurkat (derived from a patient with T cell leukemia). Mammalian cells other than human cells may be used, for example without limitation, rat, mouse, dog, horse, pig, or non-human primate cells. Non-limiting examples of non-human mammalian cells are Vero (African green monkey Chlorocebus kidney), COS-7 (African Green Monkey Kidney), GH3 (rat pituitary tumor), 9 L (rat glioblastoma), MC3T3 (mouse embryonic calvarial), C3H-10T1/2 (mouse embryonic mesenchymal), NIH-3T3 (mouse embryonic fibroblast). Animal cells, other than mammalian cells, are also contemplated including, without limitation, bird, fish, insect, or reptile cells. Even further eukaryotic cells, other than animal cells, are contemplated, for example plant cells.

Recombinant cells, comprising a magnetosome nucleic acid sequence may be advantageously used in the recombinant production of magnetosome-like structures. Recombinant magnetosome-like structures are magnetosome-like structures that do not naturally occur in a eukaryotic cell in that they may comprise a magnetosome protein or their formation may be directed by a magnetosome protein that does not naturally occur in the eukaryotic cell.

In certain aspects of the invention, a cell may be altered or modified to express a magnetosome gene encoding a magnetosome protein that does not naturally occur in the cell, and as such the cell will be considered recombinant. As is understood by one of skill in the art, a magnetosome gene May be introduced into a cell using any known technique, for example, microinjection, electroporation, viral transfection, lipofectamine transfection, calcium phosphate precipitation and the like. In certain non-limiting examples, cells may be isolated from a eukaryotic organism, modified by introduction of a magnetosome gene, and then the modified cells may be administered or inserted in a desired location in the subject. In certain other examples, a magnetosome gene may be incorporated into an appropriate construct or vehicle, for example a viral construct, and administered or inserted in a desired location in a eukaryotic subject such that the magnetosome gene(s) is introduced and expressed in at least a portion of the cells of the subject. A magnetosome gene can include but is not limited to MagA (an iron transport gene disclosed in U.S. Pat. No. 5,861,285, the disclosure of which is incorporated herein in its entirety), MamK (a gene responsible for organizing magnetosome chains; see for example, Komeili et al. (2006) or Stephens (2006)) and MMS16 (a gene responsible for function as it involves GTPase activity; see for example, Okamura et al. (2001) or Schuler (2004)). One or more magnetosome nucleic acid sequences (for example, genomic, cDNA or functional portions thereof) can be used in the present invention as well as magnetosome-associated genes. A number of magnetosome genes can be introduced into a cell, either singly or in combination, to optimize the formation of magnetosome-like structures for use as a contrasting agent. Furthermore, magnetosome genes and magnetosome-associated genes for use in the invention can be mutated or altered prior to transfection into the cells as desired, for example for codon optimization for expression in mammalian cells. Magnetosome genes and magnetosome-associated genes can be made as fusion proteins as desired in an application, for example fusion with a targeting peptide or a therapeutic peptide.

A magnetosome nucleic acid may be any nucleic acid molecule of, for example. cDNA, genomic DNA, synthetic DNA or RNA origin or suitable combinations thereof and which may be based on a complete or partial naturally occurring nucleic acid sequence encoding a magnetosome protein. A magnetosome protein may be any protein of, for example, recombinant or synthetic origin or suitable combinations thereof and which may be based on a complete or partial naturally occurring amino acid sequence encoding a magnetosome protein. A magnetosome nucleic acid or protein may be mutated or changed or derivatised in any manner desired (for example, deletion, insertion, substitution) to produce a variant. Use of such variants in producing magnetosome-like structures is contemplated, and such a variant nucleic acid or variant protein may be mutated or changed or derivatised in any manner in comparison to a naturally occurring magnetosome nucleic acid or protein, respectively, provided that the capability of forming magnetosome-like structures is maintained. Similarly, magnetosome nucleic acids or magnetosome proteins having varying degrees of sequence identity to a corresponding naturally occurring magnetosome nucleic acid or protein sequence may be tolerated without eliminating the activity of forming magnetosome-like structures. For example, a recombinant eukaryotic cell may comprise a recombinant bacterial magnetosome protein having a sequence that is identical to a naturally-occurring form of the bacterial magnetosome protein or a variant thereof that has a sequence that is at least 80% identical to a naturally-occurring form of the bacterial magnetosome protein. As another example, a recombinant eukaryotic cell may comprise a recombinant bacterial magnetosome nucleic acid having a coding sequence that is identical to a naturally-occurring form of the bacterial magnetosome gene or a variant thereof that has a sequence that is at least 70% identical to a naturally-occurring form of the bacterial magnetosome gene. Determination of sequence identity of proteins and nucleic acids by computer based methods, as well as nucleic acid hybridization techniques for determining or identifying sequences that share high (eg., at least 70%) sequence identity are well known to the skilled person. Magnetosome genes have been cloned and sequenced from various sources and have been shown to maintain biological activity over varying degrees of sequence identity. For example, nucleic acids encoding MagA have been cloned from a variety of sources. Table 1 identifies by accession number, several non-limiting examples of MagA sequences and shows a comparison of sequence identity.

A magnetosome nucleic acid may be operably linked to control sequences, typically in the context of a suitable vector. A useful control sequence may be any nucleic acid element that is necessary or advantageous for expression of the coding sequence of the nucleic acid sequence. Each control sequence may be native or foreign to the nucleic acid sequence encoding the magnetosome protein. Such control sequences include, but are not limited to, a leader, a polyadenylation sequence, a propeptide sequence, a promoter, a signal sequence, or a transcription terminator. A suitable vector may be any vector (for example, a plasmid or virus) which can incorporate a magnetosome nucleic acid and any desired control sequences and can bring about the expression of the magnetosome nucleic acid sequence. The choice of the vector will typically depend on the compatibility of the vector with a host cell into which the vector is to be introduced. In certain examples, the vector may exist as an extrachromosomal entity, with replication being independent of chromosomal replication, for example, a plasmid, an extrachromosomal element, a minichromosome, or an artificial chromosome. In other examples, the vector may be one which, when introduced into the host cell, is integrated into the genome and replicated together with the chromosome(s) into which it has been integrated. Still other examples of vectors will be known and apparent to the skilled person.

In aspects of the invention, MagA expression in mammalian cells is correlated with an increase in cytoplasmic, dense core vesicles. MagA expression enhances the cellular uptake of iron and MagA expression facilitates cellular detection by MRI.

Furthermore, useful proteins such as enzymes and antibodies can be bound to the magnetosome-like structures. When the useful protein is a functional protein, the functional protein immobilized on the magnetosome-like structures can be magnetically controlled. Thus the function can be efficiently performed at a desired position.

TABLE 1

Examples of MagA encoding sequences

| Accession | Description | Max score | Total score | Query coverage | E value | Max ident |
|---|---|---|---|---|---|---|
| AB001696.1 | *Magnetospirillum magneticum* gene for MagA protein, complete cds, strain: AMB-1, clone: 3 | 2422 | 2422 | 100% | 0.0 | 100% |
| AP007255.1 | *Magnetospitillum magneticum* AMB-1 DNA, complete genome | 2194 | 2194 | 99% | 0.0 | 97% |
| D32253.1 | *Magnetospitillum magneticum* genes for MagA and hypothetical protein, complete cds, strain: AMB-1 | 2194 | 2194 | 99% | 0.0 | 97% |
| AB001694.1 | *Magnetospitillum magneticum* gene for MagA protein, complete cds, strain: AMB-1, clone: 10 | 2167 | 2167 | 100% | 0.0 | 96% |
| AB001698.1 | *Magnetospitillum magneticum* gene for MagA protein, complete cds, strain: MGT-1 | 1751 | 1751 | 100% | 0.0 | 90% |
| AB001699.1 | *Magnetospirillum magnetotacticum* gene for MagA protein, complete cds, strain: MS-1 | 1546 | 1546 | 100% | 0.0 | 88% |
| AF257521.1 | *Magnetospirillum magnetotacticum* MagA gene, complete cds; and RNaseHII gene, partial cds | 1541 | 1541 | 99% | 0.0 | 88% |
| AB001695.1 | *Magnetospitillum magneticum* gene for MagA protein, complete cds, strain: AMB-1, clone: 141 | 933 | 986 | 46% | 0.0 | 100% |
| AB001697.1 | *Magnetospitillum magneticum* gene for MagA protein, partial cds, strain: AMB-1, clone: 46 | 917 | 917 | 41% | 0.0 | |

In a non-limiting embodiment of the invention magA cDNA was obtained from the freshwater bacterium *Aquaspirillum* strain AMB-1 and cloned into suitable mammalian plasmid vectors using standard procedures. Magnetosome nucleic acid sequences may be expressed from mammalian (pEGFP, pcDNA3.1mycHis) or yeast (pG-BKT7, pACT2) vectors, for example. These plasmids use the CMV and ADH1 promoters, respectively. Transfection of magA constructs was done into the rat pancreatic islet cell line INS-1, the mouse neuroblastoma cell line N2A, and canine bone marrow stromal cells. Compared to SPIO (super paramagnetic iron oxide) transfected INS-1 or N2A cells, in which the iron particles are compartmentalized by a dextran-coated shell, magA transfected cells show similar compartmentalization, using membrane-bound vesicles instead of the dextran shell (FIG. 2). These data demonstrate that endogenous cellular contrast can be achieved in mammalian cells through the expression of a magnetosome gene that forms a magnetosome-like structure as a contrast agent.

Characterization of magA expression from pEGFP was confirmed by fluorescence microscopy (FIG. 2A) and Western blot using antibody to GFP. As well, electron microscopy was used to visualize electron dense vesicles. Magnetosome-like structures were identified as dense core vesicles distinct from the morphology of secretory granules in endocrine cells (FIGS. 2C, D). The electron dense core of these vesicles is consistent with an increase in iron content in MagA transfected cells, as identified by Prussian blue stain (FIG. 2B).

Magnetosome vesicles may contain biomineralized iron, or may be empty, depending on whether or not cells are grown in an iron-rich or iron-depleted environment (Komeili et al., 2006). The effect of recombinant magnetosome nucleic acid expression in eukaryotic cells resulting in recombinant magnetosome structures that enclose iron-containing particles can be seen over a broad range of iron concentrations, including for example and without limitation, concentrations ranging from at least about 0.1 micromolar and higher. For example, MagA expressing cells cultured in media having from about 0.25 micromolar to about 250 micromolar iron can produce magnetosome-like structures enclosing suitable amounts of iron. In other examples, the iron concentration may range from about 0.40 micromolar to about 200 micromolar. Typically, any physiological eukaryotic environment provides sufficient iron for recombinant magnetosome nucleic acid expression to result in a magnetosome-like structure enclosing useful levels of iron. Furthermore, non-toxic iron concentrations that are higher than physiological iron concentrations may be used. Simply as a further illustrative concentration range, and without limitation, useful iron concentrations may range from about 0.1 micromolar to about 500 micromolar. Even higher concentrations may be used, if desired.

Imaging or analysis of magnetosome-like structures may be performed using a variety of techniques for example electron microscopy, MRI, X-ray imaging, and the like. Magnetic resonance imaging (MRI) requires cellular or tissue contrast to distinguish given morphology or anatomy. Superparamagnetic iron is an ideal contrast agent. Magnetite crystals synthesized within bacterial magnetosomes provide permanent, single-magnetic-domain particles, suitable for MRI. As has been shown in the present disclosure, recombinant magnetosome-like structures produced in eukaryotic cells provide permanent, single-magnetic-domain particles, suitable for MRI. Nuclear medicine imaging techniques, that rely on radioisotopes, can be paired with MRI to provide hybrid imaging that combines the sensitivity of radionuclides with the superior resolution of magnetic resonance. One example is, PET (Positron Emission Tomography)/MRI technology. Another example, is a PET/CT (x-ray Computed Tomography) hybrid imaging systems. Furthermore, eukaryotic cells comprising magnetosome-like structures may be useful for registration of MRI with CT. Both MRI and CT can provide anatomical information even though the methods rely on different premises.

Aspects of the invention have particular use with eukaryotic cells that express or over express one or more magnetosome proteins as magnetosome-like structure contrast agents permitting in vivo or non-invasive MRI or x-ray imaging studies to follow the localization, proliferation, and long-term tracking of cells comprising magnetosome-like structures. These cells may be tissue specific and permit non-invasive in vivo imaging of specific physiological functions. Since the magnetosome-like structures are localized and susceptible to directed energies, other potential uses include, but are not limited to, creation of directed hyperthermia (Hergt et al., 2005), for example MR guided ultrasound to generate thermal ablation, magnetic ablation treatment through increased power absorption rates with electric or magnetic transmitters (Hilger et al., 2002), magnetomechanical stimulation (Lin et al., 1999), magnetically guided transport of drugs (Schuler and Frankel, 1999) or bacterial detoxification of environmental contamination (bioremediation).

Aspects of the present invention have further wide potential clinical uses such as described below.

Cardiac Stem Cell Transplantation

After a heart attack, the patient is often left with a large amount of scar tissue in place of normally contracting heart muscle. If the amount of tissue is large enough, the patient's physical activity is limited and they may go on to chronic heart failure and death. Heart transplantation remains the treatment of choice, but the number of available organs will never meet more than a small fraction of the growing demand. As another treatment option, stem cell therapy to regenerate the damaged heart is being aggressively pursued. What is needed is a way to image, quantify and monitor the progression of transplanted stem cells from undifferentiated to differentiated states, as the cells repopulate the scar tissue with normally functioning heart tissue. The use of magnetosome-like structures to track the progress of tissue regeneration has both research and therapeutic applications.

a) Prior to transplantation, stem cells would be transfected with magnetosome-producing genes to follow the fate of the transplanted cells by MR imaging. This type of experiment would follow the original stem cell population, from transplantation to lineage commitment and differentiation, by the production of magnetosome-like structures.

b) To monitor the switch from proliferation to differentiation, cells would be transfected with magnetosome constructs in which the promoter responds to stage-specific differentiation signals. This type of experiment would indicate early and late events in stem cell differentiation and localize these events within the injured heart.

c) Different types of cellular differentiation would be monitored by transfecting stem cells with magnetosome constructs that respond to transcription factors present in specific types of cardiac cells, such as smooth muscle cells, endothelial cells or myocytes. This type of experiment would indicate the number of stem cells needed for successful treatment and how efficient stem cells are at producing functional myocardium.

d) The rate of stem cell loss after transplantation would also be monitored by placing magnetosome genes behind promoters sensitive to apoptotic signals or co-expressing magnetosomes with early markers of apoptosis. In this context, magnetosome-like structure formation would localize the extent of programmed cell death that undermines stem cell therapy in a given organ.

e) In cardiac cells, the protective effects of heat shock proteins (Lin et al., 1999) constitute a natural defense against ischemia through preconditioning. This protective mechanism will be monitored in vivo by placing magnetosome gene(s) under the control of an inducible heat shock promoter to understand the timing and location of this survival mechanism.

f) The regulation of magnetosome-like structure production would be genetically controlled by the expression of inhibitory factors that prevent magnetosome proteins from assembling or functioning. These negative regulators would be under selective promoter control, responding to exogenously administered antibiotic or pheromone, or targeted directly to the magnetosome by virtue of its magnetic properties.

Monitoring Gene Therapy in Diabetes

In diabetic disorders, the pancreas fails to produce sufficient insulin for the natural absorption of glucose. Regeneration therapy of pancreatic β-islet cells, which produce insulin, may provide a cure for diabetes (Yamaoka, 2002). Various therapeutic strategies, including islet transplantation, cell-based therapy, gene therapy and drug therapy to promote β-cell formation and proliferation have been suggested. Magnetosome expression in transplanted islets or the cells used for gene or cell-based therapy would provide an endogenous monitoring system for these treatments.

a) Co-transfection of islet or stem cells with the insulin promoter driving MagA expression, to turn on magnetosome production once the transplanted cells start producing insulin, will allow functional monitoring of the regeneration therapy. This system would be valuable for in vivo as well as in vitro analyses.

b) Evidence of glucose-stimulated insulin secretion, characteristic of pancreatic beta cells, will be obtained from magnetosome-protein expressing cells in an insulin target tissue. In response to a rise in serum insulin, cells within the target tissue that express magnetosome genes off an insulin-sensitive promoter will be labelled with magnetite crystals and suitable for MR imaging. This type of system will also respond to external stimuli, such as a glucose challenge, that precipitates the secretion of insulin.

c) Transfection of stem cells or islet cells, destined for transplantation into the pancreas of diabetic animals, will be non-invasively monitored by the production of magnetosome-like structures. MR imaging will localize the cells within the target tissue, as well as any ectopic transplantation.

d) Other mammalian cells harbouring both a therapeutic gene and magnetosome gene(s) can be non-invasively monitored by MR imaging. Gene therapy will be administered by an unrelated cell that is targeted to the tissue of interest by a receptor-ligand interaction, such as binding of insulin growth factor receptor to the insulin growth factor. Thus, proteins at the plasma membranes of both cells provide a docking site, permitting localization of the gene therapy and non-invasive tracking of these magnetosome-protein expressing carrier cells.

Cancer Progression and Treatment

Evaluation of tumour progression or regression during cancer treatment is critical to determining the efficacy of the therapy and whether other treatments should be pursued. The effect of cancer therapy on the tumour will be monitored by MR imaging of immune or other cells, targeted to the tumour and transfected with magnetosome gene(s). This provides non-invasive, in vivo monitoring of the cancer.

a) Lymphocytes from the patient will be isolated and transfected with magnetosome gene(s) as well as those for tumour-specific receptors. Upon introduction of these modified cells back into the patient, MR imaging will be used to non-invasively monitor the location of magnetosome-protein expressing cells in the patient. The efficiency of tumour infiltration by the magnetosome-protein expressing cells will indicate the degree of tumour-specific recognition. Magnetosome-like structure production will provide the in vivo assay for the most appropriate tumour-specific, cell surface proteins. This assay can also be used to monitor changes in tumour-specific protein expression, as may, be related to benign versus malignant and dormant versus metastatic tumours.

b) Magnetosome-like structure expressing cells that target the tumour will be used to monitor tumour size over the course of cancer treatment. This will permit vigilant monitoring of tumour growth and aid in the timing and selection of treatment regimens.

c) Magnetosome-like structure expressing cells that target the tumour will be used to monitor metastases. The spread of cancer will be identified and localized by MR imaging of magnetosome-like structures co-expressed in cells with genes that are characteristic markers of metastasis. Non-invasive imaging of metastases will aid in directing treatment to the correct location. The production of magnetosome-like structures will also assist in distinguishing which population of tumour cells become metastatic and which remain dormant.

d) Cells that produce magnetosome-like structures that target the tumour will be used to direct magnetic field effects, such as hyperthermia, or delivery of other treatments to the tumour.

e) Cells that produce magnetosome-like structures that target the tumour will be used to colocalize tumour antigens, or other tumour-associated proteins, that cause differentiation or apoptosis of magnetosome-expressing cells, in response to tumour progression or arrest. These changes in magnetosome-expressing cells may reflect the presence or absence of growth factors, or other signal transduction activity, in the neighbouring tumour cells.

f) Since magnetosome-like structure formation/expression is recapitulated with each cell division, cells from tumour biopsies can be cultured in vitro, transfected with magnetosome gene(s), and studied over the long-term in laboratory animal models. In this way, MR imaging of magnetosome-expressing cells can be used to develop novel treatments for specific types of cancer.

g) Magnetosome-expressing cells that target the tumour can be cultured and implanted under iron-deficient conditions, such that tumour angiogenesis will be monitored by the increase in MR signal paralleling increases in capillary bed formation.

h) It is proposed to (1) follow molecular events in metastasizing cells using a novel reporter gene recently developed in our laboratory (Goldhawk, McCreary et al. 2006; Prato, Goldhawk et al. 2006), (2) develop quantitative tracking methods by co-labeling cells in vitro with a radioisotopic imaging agent which can report the number of transplanted cells remaining viable (Jin, Kong et al. 2006; Stodilka, Blackwood et al. 2006; Stodilka, Blackwood et al. 2006), and (3) demonstrate this methodology in a well-established mouse brain metastasis model (Heyn, Ronald et al. 2006).

To develop MagA as a reporter gene for MRI and cancer therapy, constitutive MagA expression will be compared with that of a MagA reporter construct, driven by activation of a relevant oncogenic promoter. Transfected cells may be monitored in vitro by MRI (Goldhawk, McCreary et al. 2006) and SPECT (single photon emission computed tomography; Tai, Nguyen et al. 2006), and analyzed for magnetosome-like structures by electron microscopy, energy dispersive x-ray, and immunofluorescence microscopy.

The efficacy of MagA labelling in mouse will be compared to that of $^{111}$Indium-tropolone, which has been used extensively in a canine, cardiac stem cell transplantation model (Blackwood, Kong et al. 2006; Jin, Kong et al. 2006). Hence, both large and small animal imaging are feasible, with the registration of CT (x-ray computed tomography) and MRI images providing the necessary anatomical link between the SPECT radiotracer signal and MagA signal voids generated by MRI. Estimates of cell number may also be correlated to histological analysis of tissue ex vivo, at designated time points.

Thus MagA may be used as a contrast agent for molecular imaging with MRI, with the design of a MagA reporter probe, and demonstrate its application in a cancer cell model. Non-invasive imaging of a cellular probe which is subject to gene regulation may provide information about cell localization, migration, viability, proliferation and state of differentiation. This will have a broad application in tracking cells of all types, from metastasis of breast tumours (Chambers, Groom et al. 2002), to function of pancreatic islet cells (Goldhawk, McCreary et al. 2006) in diabetes and fate of bone marrow stem cells (Jin, Kong et al. 2005) being developed for cardiac cell therapy. Once the fate of transplanted cells is understood, further therapies may be developed to optimize treatment of human disease.

Developmental Biology

Magnetosome-protein expression in mammalian or other germ cells leading to magnetosome-like structure formation will be used to monitor development of the fetus, including transgenic animal development, in which specific genes are either overexpressed or knocked out. This research will contribute to our understanding of both normal and aberrant development by providing a method for non-invasive, in vivo imaging of the cellular changes that accompany growth and differentiation of an organism. Magnetosome expression during development will be used to identify the location and temporal manifestation of birth defects by MR imaging so that preventative measures can be developed and implemented.

a) Oocytes will be transfected with magnetosome gene(s), fertilized and implanted into pseudopregnant females. Fetal development will be monitored by MR imaging of magnetosome-like structures as the zygote evolves into pre-implantation embryo, and transitions through implantation and organogenesis. This non-invasive method of monitoring development will be applicable to both vertebrate and invertebrate animals.

b) Select aspects of development will be examined by placing magnetosome gene(s) behind organ-specific promoters, such as the nestin promoter used for tracking neural development. In this way the onset of specific tissue formation can be identified and correlated with other gene expression and nascent morphology of the organism.

c) Transgenic constructs bearing magnetosome gene(s) will be inserted into the host genome so as to (1) create a nondisruptive addition to the genome, (2) replace nonessential genes, or (3) knock-out specific target genes. Specific genetic constructs can be engineered to control the embryonic expression of magnetosomes by diet, molecular agonist or antagonist. Selective expression of magnetosome-like structures during development will be used to mark the onset of particular developmental events, and may be linked to other gene expression, such as pancreatic insulin or lung surfactant production.

Plant Research

The development of hardier crops, able to withstand environmental extremes has been facilitated by research aimed at creating transgenic plants. Magnetosome-like structure formation in plants will be used both in research and industry to improve, and add versatility to, crop production.

a) To assist plant growth in space, magnetosome-like structure formation will impart magnetic properties to plants, allowing them to grow in the proper orientation in the absence of gravity, that is toward a magnet.

b) Creation of a magnetosome-like structure forming line of grape vines will assist in the development of roots that can survive during the winter frosts found in colder climates. Transgenic plants that respond to magnetothermal exposure will make northern climates more arable and therefore habitable. This technology will be adapted to other essential crops, providing a safeguard from unseasonal frost and potentially introducing winter crops to regions that traditionally experience a shorter growing season.

Functional Molecular Imaging

Many features of cellular function are defined by the nature of the cell's protein-protein interactions. The expression of magnetosome gene(s), to provide magnetosome-like structures as contrast agents to enhance cell contrast for MR imaging, provides an assay for cell specific activity. Combining magnetosome gene expression with protein-protein interactions will expand the development of functional molecular imaging.

a) The yeast two-hybrid screen employs multiple reporter genes, each responding to particular regions of the GAL upstream activating sequence that regulates galactose in yeast. The modular nature of the GAL4 transcription factor DNA binding domain and activation domain has been adapted for the detection of protein binding interactions. Activation of gene transcription is determined by protein-protein interaction, where the binding partners are fused to either the GAL4 binding domain or activation domain. Magnetosome gene expression will be linked to activation of the GAL promoter, such that a given protein-protein interaction can be identified by MR imaging.

b) Whereas fluorescence activated cell sorting (FACS) is used to separate transfected cells based on the expression of a fluorescent tag, magnetosome gene expression will be used to separate transfected cells based on their acquired magnetic properties.

c) Magnetosome gene expression in nonmagnetic bacteria will couple magnetic properties to other bacterial functions, whether for genetic engineering or bioremediation. Molecular cloning of therapeutically valuable proteins, such as recombinant insulin used to treat type I diabetes, or recombinant viral proteins used for vaccines, in magnetosome expressing host cells or from magnetosome expression vectors, will provide another method for selecting clones of interest based on magnetic resonance imaging.

d) The gene(s) that contribute to formation of magnetosome vesicles are distinct from the gene(s) that induce magnetosomes to cluster along the plasma membrane. The MR signal monitors the subcellular organization of magnetosomes by the change in signal intensity.

Carbon Fixation by Diatoms

Carbon fixation by phytoplankton is believed to correspond to half the earth's total carbon fixation, with half of that exported to the deep ocean as sinking particles. This apparently regulates atmospheric $CO_2$ and hence climate. However, at present diatom fixation of carbon is considerably less than that in the past, particularly during former ice ages. This is believed to be related to a low concentration of iron available to diatoms in some 30% of the oceans. It has been suggested that iron "fertilization" of the oceans could increase carbon fixation by diatoms and hence counter global warming. However, before embarking on such an endeavour more needs to be understood regarding copper biochemistry and how it affects iron biochemistry. Iron-limited diatoms have a higher affinity or demand for copper, and vice versa. Hence, before supplementing iron-limited diatoms, knowledge of the iron-copper relationship is required. Magnetosome-like structure formation in diatoms would assist in directing diatoms to parts of the oceans in which they are low in concentration and $CO_2$ fixation is diminished.

When introducing elements disclosed herein, the articles "a", "an", "the", and "said" are intended to mean that there are one or more of the elements unless the context dictates otherwise. For example, the term "a compound" and "at least one compound" may include a plurality of compounds, including mixtures thereof. The terms "comprising", "having", "including" are intended to be open-ended and mean that there may be additional elements other than the listed elements.

The above disclosure generally describes preferred embodiments of the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

Example 1

MagA cDNA was obtained from magnetotactic bacteria by RT PCR and cloned into pCR2.1-TOPO. The insert was sequenced, subcloned into pEGFP and pcDNA3.1mycHis, and transfected into INS-1, N2A and bone marrow stromal cells using Lipofectamine 2000, according to the manufacturer's protocol. Prior to harvesting, transfected cells were cultured in media supplemented with 250 μM ferric nitrate, then mounted in Nunc 96-well ELISA wells, embedded between 4% and 1% gelatin, and overlaid with 2% gelatin. FIG. 2A shows the expression of EGFP-MagA fusion protein in INS-1 and N2A cells. FIGS. 2C and 2D shows the dense core vesicles formed in INS-1 cells, subsequent to MagA overexpression. FIG. 2E shows the results of MRI of MagA expressing INS-1 cells. Areas of signal loss represent the formation of magnetosome-like structures in transfected cells.

Example 2

MagA was expressed as a fusion protein from pEGFP-C3. Lipofectamine transfection was done of INS-1 rat islet cells and N2A mouse neuroblastoma cells. Protein expression was examined by epifluorescence microscopy. Magnetite formation was monitored by Prussian Blue stain for iron. Ultrastructural analysis was done using Transmission Electron Microscopy (TEM). Non-invasive imaging of cells was done with Magnetic Resonance Imaging (FIGS. 3-5).

Neuroendocrine and bone marrow stromal cells were transfected with an EGFP-MagA construct and examined for evidence of MagA expression, iron retention and magnetosome formation. Fluorescence microscopy showed cytoplasmic GFP fluorescence, indicating that MagA was expressed in each cell type examined. Cells expressing MagA were incubated overnight in media containing 250 μM ferric nitrate, and the extent of Prussian Blue staining indicated that MagA expression was correlated with iron retention. Electron microscopy showed the formation of electron dense, cytoplasmic vesicles in cells overexpressing MagA under iron-rich conditions. Similarly transfected cells were examined by MRI using a simple Gradient Echo with a TE of 20 ms and showed some areas of signal loss.

Taken together, these results indicate that MagA plays a role in facilitating the production of an iron-rich, membrane-bound compartment. Hence, engineering cells to manufacture iron-containing vesicles shall enable detection of molecular function with MRI providing a novel approach in multiple cell types in vitro and in vivo.

Example 3

MagA was cloned from *Magnetospirillum* sp. AMB-1 by standard techniques, and expressed as a fusion protein from pEGFP-C3. Constitutively expressed EGFP-MagA was obtained by subcloning into the Enhanced Green Fluorescent Protein plasmid, and transfecting mammalian cell lines using Lipofectamine 2000. MagA expression studies were conducted in the rat beta cell line (INS-1) and in the mouse neuroblastoma cell line (N2A). MagA expression in INS-1 is transient: cells are analyzed within 24-48 hours of transfection. Gene expression off the plasmid may be short-lived. In contrast, data collected from the mouse neuroblastoma cell line, N2A is based on stable transfection of magA in N2A: cells are subjected to 2 or more weeks of antibiotic selection before further analysis. More specifically, mouse neuroblastoma (N2A) cells were transfected using Lipofectamine 2000 and selected with Geneticin. Gene expression has usually been incorporated into the cellular genome for long-term expression.

Both transient and stably expressing cell populations were examined for green fluorescence on an Olympus IX81 inverted microscope. MagA expression was correlated with iron retention using DAB-enhanced Prussian Blue staining. Ultrastructural analysis of transfected cells was conducted using transmission electron microscopy. Non-invasive imaging of viable cells was performed by MRI on cells using an 11T (11 Tesla magnet) Bruker and simple gradient echo with a TE of 20 ms.

Fluorescence microscopy showed cytoplasmic GFP fluorescence, indicating that MagA fusion protein is expressed in each cell type examined. In cultures supplemented with ferric nitrate, the extent of Prussian Blue staining indicated that MagA expression is correlated with, iron retention. Ultrastructural analysis of transfected cells showed the formation of electron dense, cytoplasmic vesicles in cells overexpressing MagA and cultured under iron-rich conditions. High field MRI, performed on cells mounted in gelatin, showed some areas of signal loss (FIG. 6) using a simple gradient echo with a TE of 20 ms.

Example 4

N2A cells were transfected with full-length MagA (pEGFP-C3/MagA(R1) stop85W) using Lipofectamine 2000 and grown under neomycin selection. MRI was performed on cells mounted in gelatin, after culturing in the presence or absence of an iron supplement (250 μM ferric nitrate). Culture media, in the absence of an iron supplement, contains 0.25 μM ferric nitrate. Signal voids, represented by blackened areas on positive contrast images or conversely by white regions on negative contrast images, indicate the degree to which MagA expressing cells may be detected. A, E, $10^6$ cells without iron supplement (0.25 μM ferric nitrate); B, F, $10^6$ cells with iron supplement; C, G, $10^5$ cells with iron supplement; D, H, $10^4$ cells with iron supplement. Samples E and H contain strands of human hair to mark the plane of focus. Each data set (A-H) contains images captured in adjacent, axial cross-sections.

Example 5

Neuroblastoma N2A cells were transfected with either pEGFP-C3 alone or containing MagA V137E (Valine replaced with Glutamate at position 137) inserted at Eco R1. Transfected cells were selected over 2 to 3 weeks with Geneticin and cultured in media containing an iron supplement (250 μM ferric nitrate). Approximately $10^6$ cells were mounted in a gelatin mold and imaged at high field strength (11 Tesla) by MRI. FIG. 8A shows MR imaging of a gelatin mold alone in the absence of cells, in positive and negative contrast images, at 2 different focal planes. The gelatine mold background is seen to be minimal. FIG. 8B shows the background provided by 1 million cells cultured with an iron supplement expressing vector alone without MagA, in positive and negative contrast images, at 2 different focal planes. FIGS. 8C, 8D, and 8E pertain to cells comprising a vector with MagA insert and having been cultured in iron supplemented media. FIGS. 8C and 8D each show numerous signal voids, from cells comprising vector with MagA V137E insert, for 4 different focal planes in positive contrast (FIG. 8C) and negative contrast (FIG. 8D) images, while FIG. 8E shows spin echo imaging at these 4 focal planes. Spin echo imaging sequences at each focal plane indicate that signal voids cannot be attributed to air pockets. Human hair marks the focal plane.

The results herein suggest that expression of magnetosome nucleic acids and production of magnetosome proteins in mammalian cells is associated with (a) iron retention and the formation of dense core vesicles, and (b) magnetic properties useful as a contrast agent. These data identify the potential use of magnetosome nucleic acids as a reporter gene probe that will function as an MRI contrast agent. Magnetosome gene expression systems for MRI are useful for non-invasive detection of molecular events in cells, tissues and animals.

REFERENCES

Arbab, A., Bashaw, L., Bradley, R., Jordan, E., Bulte, J., and Frank, J. (2003). Intracytoplasmic tagging of cells with ferumoxides and transfection agent for cellular magnetic resonance imaging after cell transplantation: methods and techniques. Transplantation 76, 1123-1130.

Bauerlein, E., Schuler, D., Reszka, R., and Pauser, S. (2001). Specific magnetosome, method for the production and use thereof, U. P. Office, ed. (United States: Max-Delbruck-Centrum fur Molekulare Medizin and Max-Planck-Gesellschaft zur Forderung der Wissenschaften E.V.).

Bauerlein, E., Schuler, D., Reszka, R., and Pauser, S. (2002). Magnetosomes, method for making and using, U. P. Office, ed. (United States).

Bazylinski, D., and Frankel, R. (2004). Magnetosome formation in prokaryotes. Nat Rev Microbiol 2, 217-230.

Bulte, J., Douglas, T., Mann, S., Frankel, R., Moskowits, B., Brooks, R., Baumgartner, C., Vymazal, J., and Frank, J. (1994). Magnetoferritin. Biomineralization as a novel molecular approach in the design of iron-oxide-based magnetic resonance contrast agents. Invest Radiol 29 Suppl. 2, S214-S216.

Chalfie, M., Tu, Y., Euskirchen, G., Ward, W., and Prasher, D. (1994). Green fluorescent protein as a marker for gene expression. Science 263, 802-805.

Dhanvantari, S., Foster, P., White, D., McCreary, C., Nguyen, B., Mugimba, A., Chan, K., Hoffman, L., McGirr, R., Kovacs, M., and Wells, R. (2006). Cellular and molecular imaging of pancreatic islet cells, In Keystone Symposium, Towards Understanding Islet Biology.

Dhanvantari, S., Tai, J.-H., White, D., Heyn, C., Rutt, B., and Foster, P. (2004). Single cell magnetic resonance imaging of beta cells, In Annual Meeting of the Canadian Diabetes Association.

Genove, G., DeMarco, U., Xu, H., Goins, W., and Ahrens, E. (2005). A new transgene reporter for in vivo magnetic resonance imaging. Nat Med 11, 450-454.

Grünberg, K., Wawer, C., Tebo, B., and Schüler, D. (2001). A large gene cluster encoding several magnetosome proteins is conserved in different species of magnetotactic bacteria. Appl Env Microbiol 67, 4573-4582.

Hautot, D., Pankhurst, Q., Khan, N., and Dobson, J. (2003). Preliminary evaluation of nanoscale biogenic magnetite in Alzheimer's disease brain tissue. Proc R Soc Lond B (Suppl) 270, S62-S64.

Herborn, C., Papanikolaou, N., Reszka, R., Grunberg, K., Schüller, D., and Debatin, J. (2003). Magnetosomes as biological model for iron binding: relaxivity determination with MRI. Rofo: Fortschritte auf dem Gebiete der Rontgenstrahlen und der Nuklearmedizin 175, 830-834.

Hergt, R., Hiergeist, R., Zeisberger, M., Schüler, D., Heyen, U., Hilger, I., and Kaiser, W. (2005). Magnetic properties of bacterial magnetosomes as potential diagnostic and therapeutic tools. J Magn Magn Mater 293, 80-86.

Hilger, I., Fruhauf, K., Andra, W., Hiergeist, R., Hergt, R., and Kaiser, W. (2002). Heating potential of iron oxides for therapeutic purposes in interventional radiology. Acad Radiol 9, 198-202.

Kirschvink, J. (1989). Magnetite biomineralization and geomagnetic sensitivity in higher animals: an update and recommendations for future study. Bioelectromagnetics 10, 239-259.

Kirschvink, J., Kobayashi-Kirschvink, A., and Woodford, B. (1992). Magnetite biomineralization in the human brain. Proc Nat Acad Sci USA 89, 7683-7687.

Kirschvink, J., Walker, M., and Diebel, C. (2001). Magnetite-based magnetoreception. Curr Opin Neurobiol 11, 462-467.

Komeili, A., Li, Z., Newman, D., and Jensen, G. (2006). Magnetosomes are cell membrane invaginations organized by the actin-like protein MamK. Science 311, 242-245.

Lin, H., Blank, M., and Goodman, R. (1999). A magnetic field-responsive domain in the human HSP70 promoter. J Cell Biochem 75, 170-176.

Matsunaga, T. (2000). Protein-bound magnetic particles and process of producing the same, U.S. P. Office, ed. (United States: TDK Corporation).

Matsunaga, T., Nakamura, C., Burgess, 3., and Sode, K. (1992). Gene transfer in magnetic bacteria: transposon mutagenesis and cloning of genomic DNA fragments required for magnetosome synthesis. 3 Bacteriol 174, 2748-2753.

Matsunaga, T., Takeyama, H., and Okamura, Y. (2004). Magnetic particle membrane-specific protein, U.S. P. Office, ed. (United States).

Okamura, Y., Takeyama, H., and Matsunaga, T. (2001) A magnetosome-specific GTPase from the magnetic bacterium *Magnetospirillum magneticum* AMB-1. J. Biol. Chem. 276, 48183-48188.

Ritz, T., Thalau, P., Phillips, 3., Wiltschko, R., and Wiltschko, W. (2004). Resonance effects indicate a radical-pair mechanism for avian magnetic compass. Nature 429, 177-180.

Schüller, D. (April 2004-March 2006a). Main themes of scientific work, In Biannual Report, Department of Microbiology (Max Planck Institute for Marine Biology), pp. 79-80.

Schüler, D. (April 2004-March 2006b). Survey of major projects, In Biannual Report, Research Concept (Max Planck Institute for Marine Biology), pp. 13-14.

Schüler, D. (2004) Molecular analysis of a subcellular compartment: the magnetosome membrane in *Magnetospirillum gryphiswaldense*. Arch. Microbiol. 181, 1-7.

Schüler, D., and Frankel, R. (1999). Bacterial magnetosomes: microbiology, biomineralization and biotechnological applications. Appl Microbiol Biotechnol 52, 464-473.

Southward, C., and Surette, M. (2002). The dynamic microbe: green fluorescent protein brings bacteria to light. Mol Microbiol 45, 1191-1196.

Stephens, C. (2006) Bacterial cell biology: managing magnetosomes. Curr. Biol. 16, R363-R365.

Van Roessel, P., and Brand, A. (2002). Imaging into the future: visualizing gene expression and protein interactions with fluorescent proteins. Nat Cell Biol 4, E15-E20.

Walker, M., Quinn, T., Kirschvink, J., and Groot, C. (1988). Production of single-domain magnetite throughout life by sockeye salmon, Oncorhynchus nerka. J Exp Biol 140, 51-63.

Yamaoka, T. (2002). Regeneration therapy of pancreatic beta cells: towards a cure for diabetes? Biochem Biophys Res Comm 296, 1039-1043.

Blackwood, K., H. Kong, et al. (2006). In vivo evaluation of thymidine kinase overexpression to track canine bone marrow stromal cells using dual isotope SPECT. *Fifth Annual Meeting of the Society for Molecular Imaging*. Hawaii, Mol. Imaging. 5: 234.

Chambers, A. F., A. C. Groom, et al. (2002). "Dissemination and growth of cancer cells in metastatic sites." *Nat. Rev. Cancer.* 2: 563-572.

Goldhawk, D., C. McCreary, et al. (2006). Magnetic resonance imaging of cells overexpressing MagA, an iron transporter involved in magnetosome formation. *Fifth Annual Meeting of the Society for Molecular Imaging*. Hawaii, Mol. Imaging. 5: 294.

Heyn, C., J. A. Ronald, et al. (2006). "In vivo MRI of cancer cell fate at the single-cell level in a mouse model of breast cancer metastasis to the brain." *Magn. Reson. Med.* 56: 1001-1010.

Jin, Y., H. Kong, et al. (2005). "Determining the minimum number of detectable cardiac-transplanted $^{111}$In-tropolone labelled bone-marrow-derived mesenchymal stem cells by SPECT." *Phys. Med. Biol.* 50: 4445-4455.

Jin, Y., H. Kong, et al. (2006). Cardiac transplanted $^{111}$In-tropolone-labelled autologous mesenchymal stem cells: in vivo radiotracer kinetics. *Fifth Annual Meeting of the Society for Molecular Imaging*. Hawaii, Mol. Imaging. 5: 403.

Komeili, A., Z. Li, et al. (2006). "Magnetosomes are cell membrane invaginations organized by the actin-like protein MamK." *Science* 311: 242-245.

Matsunaga, T., C. Nakamura, et al. (1992). "Gene transfer in magnetic bacteria: transposon mutagenesis and cloning of genomic DNA fragments required for magnetosome synthesis." *J. Bacteriol.* 174: 2748-2753.

Prato, F., D. Goldhawk, et al. (2006). Provisional patent application No. 60/811,784. U.S. P. Office. USA.

Stodilka, R., K. Blackwood, et al. (2006). Large animal hybrid SPECT/CT using a small field-of-view gamma camera: proof of principle for monitoring cardiac transplanted stem cells.

*Fifth Annual Meeting of the Society for Molecular Imaging*. Hawaii, Mol. Imaging. 5: 418.

Stodilka, R., K. Blackwood, et al. (2006). Performance of hybrid multi-spectral SPECT/CT in tracking transplanted cells in a canine model. *Fifth Annual Meeting of the Society for Molecular Imaging*. Hawaii, Mol. Imaging. 5: 407.

Tai, J. H., Nguyen, et al. (2006) Imaging pancreatic islet cell gene expression using dual-isotope SPECT/CT. *Tenth Annual Meeting of the Canadian Diabetes Association*. Toronto.

Although preferred embodiments of the invention have been described herein in detail, it will be understood by those skilled in the art that variations may be made thereto without departing from the spirit of the invention.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09556238B2). An electronic copy of the "Sequence Listing" will also be available from the USPTO upon request and payment of the fee set forth in 37 CFR 1.19(b)(3).

We claim:

1. A method for modifying a cell to express a magnetosome-like structure where previous to said modification the cell does not express a magnetosome-like structure, the method comprising:
   transfecting the cell with a construct comprising one or more magnetosome genes under the control of a promoter, said one or more magnetosome genes encoding at least one magnetosome transmembrane protein; and
   subjecting the cell to an environment containing iron;
   wherein the cell is selected from embryonic stem cells, islet cells, neuroblastoma cells, bone marrow stromal cells, breast cancer cells, glioblastoma cells, glioma cells, cervical cancer cells, promyelocytic leukemia cells, lung cancer cells, pituitary tumor cells, and T cell leukemia cells;
   wherein, previous to said modification, the cell did not express a magnetosome-like structure, and after said modification, the cell expresses a magnetosome-like structure comprising a lipid bilayer, an internal, iron containing region, and at least one of said magnetosome transmembrane protein within its lipid bilayer, wherein the at least one magnetosome transmembrane protein is an iron transport protein, and wherein said one or more magnetosome genes is MagA, wherein the isolated cell excludes a human embryonic stem cell.

2. The method of claim 1, wherein the magnetosome-like structure is further isolated from the cell.

3. An isolated cell made by the method of claim 1.

4. The cell of claim 3, wherein said magnetosome transmembrane protein is comprised within a fusion protein.

5. The cell of claim 4, wherein said fusion protein comprises MagA or a variant thereof and a polypeptide selected from the group consisting of a therapeutic polypeptide, a carrier polypeptide, and a targeting polypeptide.

6. The cell of claim 3, wherein said cell is a mammalian cell.

7. The cell of claim 3, wherein said cell is a mammalian cell selected from the group consisting of human, rat, mouse, dog, pig, and horse.

8. The cell of claim 6, wherein said one or more nucleic acid sequences is codon optimized for expression in mammalian cells.

9. The cell of claim 3, wherein said one or more nucleic acid sequences is codon optimized for expression in mammalian cells.

10. The method of claim 1, wherein said cell is an embryonic stem cell.

11. The method of claim 1, wherein said cell is an islet cell.

12. The method of claim 1, wherein said cell is a neuroblastoma cell.

13. The method of claim 1, wherein said cell is a breast cancer cell.

14. The method of claim 1 wherein the one or more magnetosome genes comprises two or more magnetosome genes.

15. The method of claim 14 wherein the two or more magnetosome genes are MamK and MagA.

16. A method of imaging a collection of cells or a tissue, said collection of cells or tissue comprising cells of claim 3, and further comprising detecting the presence of iron particles within the cells.

17. A method of claim 16 wherein the detecting of the presence of iron particles comprises magnetic resonance imaging.

18. A method of claim 16 wherein the detecting of the presence of iron particles comprises X-ray CT.

19. A contrast agent comprising the cell of claim 3.

20. A method of detecting the contrast agent of claim 19 comprising applying a magnetic or electromagnetic field to said contrast agent.

* * * * *